US010850118B2

(12) United States Patent
Lutz et al.

(10) Patent No.: US 10,850,118 B2
(45) Date of Patent: Dec. 1, 2020

(54) METHODS AND DEVICES FOR MINIMALLY-INVASIVE DELIVERY OF RADIATION TO THE EYE

(71) Applicant: Salutaris Medical Devices, Inc., Tucson, AZ (US)

(72) Inventors: Wendell Lutz, Tucson, AZ (US); Russell J. Hamilton, Tucson, AZ (US); Thomas C. Cetas, Tucson, AZ (US); Laurence J. Marsteller, Tucson, AZ (US); Timothy Shriver, Vail, AZ (US); Samuel S. Hyman, Tucson, AZ (US)

(73) Assignee: SALUTARIS MEDICAL DEVICES, INC., Tucson, AZ (US)

( * ) Notice: Subject to any disclaimer, the term of this patent is extended or adjusted under 35 U.S.C. 154(b) by 194 days.

(21) Appl. No.: 15/871,756

(22) Filed: Jan. 15, 2018

(65) Prior Publication Data

US 2018/0133509 A1 May 17, 2018

Related U.S. Application Data

(60) Division of application No. 14/486,401, filed on Sep. 15, 2014, now Pat. No. 9,873,001, which is a (Continued)

(51) Int. Cl.

| | |
|---|---|
| ***A61N 5/10*** | (2006.01) |
| ***A61B 1/06*** | (2006.01) |
| ***A61F 9/00*** | (2006.01) |

(52) U.S. Cl.
CPC .............. *A61N 5/1017* (2013.01); *A61B 1/06* (2013.01); *A61N 5/1007* (2013.01); *A61F 9/00* (2013.01);
(Continued)

(58) Field of Classification Search
CPC .... A61N 5/10–1084; A61N 2005/1019; A61N 2005/1024
See application file for complete search history.

(56) References Cited

U.S. PATENT DOCUMENTS

| | | | |
|---|---|---|---|
| 2,309,302 | A | 1/1943 | Butler et al. |
| 2,559,793 | A | 7/1951 | Pregel |

(Continued)

FOREIGN PATENT DOCUMENTS

| | | | |
|---|---|---|---|
| AU | 323700 | S | 1/2009 |
| AU | 323701 | S | 1/2009 |

(Continued)

OTHER PUBLICATIONS

Raghava et al.; Periocular routes for retinal drug delivery, 2004, pp. 99-114, Ashley Publications.

(Continued)

*Primary Examiner* — Catherine B Kuhlman
(74) *Attorney, Agent, or Firm* — Nguyen Tarbet LLC

(57) ABSTRACT

Methods and devices for minimally-invasive delivery of radiation to the eye (such as the posterior portion of the eye) including cannula systems with multiple treatment positions and/or multiple channels in the distal tip of the cannula systems. The channels can accommodate emanating sources and exposing a target at various treatment positions. The emanating sources may be annulus-shaped.

16 Claims, 18 Drawing Sheets

600
614
116
616,
610
612
617
401
114
112
(sclera-contacting surface)
100

Related U.S. Application Data continuation-in-part of application No. 13/872,941, filed on Apr. 29, 2013, now abandoned, and a continuation-in-part of application No. 13/953,528, filed on Jul. 29, 2013, now abandoned, and a continuation-in-part of application No. 13/111,780, filed on May 19, 2011, now Pat. No. 8,608,632, and a continuation-in-part of application No. 13/111,765, filed on May 19, 2011, now Pat. No. 8,602,959, and a continuation-in-part of application No. 12/917,044, filed on Nov. 1, 2010, now abandoned, and a continuation-in-part of application No. 14/011,516, filed on Aug. 27, 2013, now Pat. No. 9,056,201, which is a continuation-in-part of application No. 13/953,528, filed on Jul. 29, 2013, now abandoned, and a continuation-in-part of application No. 13/872,941, filed on Apr. 29, 2013, now abandoned, and a continuation-in-part of application No. 13/742,823, filed on Jan. 16, 2013, now Pat. No. 8,597,169, said application No. 13/111,780 is a continuation-in-part of application No. 12/497,644, filed on Jul. 3, 2009, now abandoned, said application No. 13/742,823 is a continuation-in-part of application No. 12/497,644, filed on Jul. 3, 2009, now abandoned, which is a division of application No. 12/350,079, filed on Jan. 7, 2009, now Pat. No. 8,430,804, said application No. 13/872,941 is a continuation-in-part of application No. 12/350,079, filed on Jan. 7, 2009, now Pat. No. 8,430,804.

(60) Provisional application No. 61/877,765, filed on Sep. 13, 2013, provisional application No. 61/676,783, filed on Jul. 27, 2012, provisional application No. 61/376,115, filed on Aug. 23, 2010, provisional application No. 61/347,233, filed on May 21, 2010, provisional application No. 61/347,226, filed on May 21, 2010, provisional application No. 61/257,232, filed on Nov. 2, 2009, provisional application No. 61/047,693, filed on Apr. 24, 2008, provisional application No. 61/035,371, filed on Mar. 10, 2008, provisional application No. 61/033,238, filed on Mar. 3, 2008, provisional application No. 61/010,322, filed on Jan. 7, 2008.

(52) U.S. Cl.
CPC ................ *A61M 2210/0612* (2013.01); *A61N 2005/1008* (2013.01); *A61N 2005/1024* (2013.01)

(56) References Cited

U.S. PATENT DOCUMENTS

D183,820 S 10/1958 Yohe
3,169,527 A 2/1965 Sheridan
3,662,882 A 5/1972 Obermayer
D235,171 S 5/1975 Boone
D235,172 S 5/1975 Boone
D236,920 S 9/1975 Sheridan
3,974,322 A 8/1976 Drabkina
4,248,354 A 2/1981 Metzger
4,300,557 A 11/1981 Refojo et al.
D272,089 S 1/1984 Glassman
4,925,450 A 5/1990 Imonti et al.
4,976,266 A 12/1990 Huffman et al.
5,007,689 A 4/1991 Kelly et al.
5,109,844 A 5/1992 de Juan, Jr. et al.
5,127,831 A 7/1992 Bab
5,167,647 A 12/1992 Wijkamp et al.
5,199,939 A 4/1993 Dake et al.
D340,111 S 10/1993 Yoshikawa
D342,313 S 12/1993 Hood et al.
D345,417 S 3/1994 Sharipov
D347,473 S 5/1994 Nitzsche
5,342,283 A 8/1994 Good
5,364,374 A 11/1994 Morrison et al.
5,392,914 A 2/1995 Lemieux et al.
5,399,298 A 3/1995 Kelly et al.
5,407,441 A 4/1995 Greenbaum
5,637,073 A 6/1997 Freire
D390,656 S 2/1998 Linder
5,871,481 A 2/1999 Kannenberg et al.
5,893,873 A 4/1999 Rader et al.
5,935,155 A 8/1999 Humayun et al.
5,944,747 A 8/1999 Greenberg et al.
5,947,891 A 9/1999 Morrison
5,970,457 A 10/1999 Brant et al.
6,013,020 A 1/2000 Meloul et al.
6,053,900 A 4/2000 Brown et al.
6,059,714 A 5/2000 Armini et al.
D428,140 S 7/2000 Swan
6,135,984 A 10/2000 Dishler
6,149,643 A 11/2000 Herekar et al.
6,159,205 A 12/2000 Herekar et al.
6,183,410 B1 2/2001 Jacobsen et al.
6,183,435 B1 2/2001 Bumbalough et al.
6,251,060 B1 * 6/2001 Hooft ...................... A61D 7/00 600/3
6,278,975 B1 8/2001 Brant et al.
6,302,839 B1 10/2001 Chernomorsky et al.
6,402,734 B1 6/2002 Weiss
6,413,245 B1 * 7/2002 Yaacobi ................ A61F 9/0017 604/264
6,443,881 B1 9/2002 Finger
6,450,938 B1 9/2002 Miller
6,497,645 B1 * 12/2002 Halpern ............... A61N 5/1007 600/3
6,527,692 B1 3/2003 Weinberger
6,575,887 B1 6/2003 Schrayer
6,613,026 B1 9/2003 Palasis et al.
6,641,518 B2 11/2003 Wolfson et al.
6,676,590 B1 1/2004 Urick et al.
6,719,750 B2 4/2004 Varner et al.
6,749,553 B2 6/2004 Brauckman et al.
6,755,338 B2 6/2004 Hahnen et al.
D492,778 S 7/2004 Narini
6,800,076 B2 10/2004 Humayun
6,824,532 B2 11/2004 Gillis et al.
6,830,174 B2 12/2004 Hillstead et al.
6,875,165 B2 4/2005 Dejuan, Jr. et al.
6,918,894 B2 7/2005 Fleury et al.
6,958,055 B2 10/2005 Donnan et al.
6,964,653 B2 11/2005 Negron
6,977,264 B2 12/2005 Fotsch et al.
7,070,556 B2 7/2006 Anderson et al.
7,103,416 B2 9/2006 Ok et al.
7,115,607 B2 10/2006 Fotsch et al.
7,153,316 B1 12/2006 McDonald
D534,650 S 1/2007 Inman et al.
D543,626 S 5/2007 Watschke et al.
7,217,263 B2 5/2007 Humayun et al.
7,220,225 B2 5/2007 Dejuan, Jr. et al.
7,223,225 B2 5/2007 DeJuan, Jr. et al.
7,228,181 B2 6/2007 Greenberg et al.
7,252,006 B2 8/2007 Tai et al.
7,273,445 B2 9/2007 Pulido et al.
D553,738 S 10/2007 Simpson
7,276,019 B2 10/2007 DeJuan, Jr. et al.
7,308,487 B1 12/2007 Dansie et al.
7,321,796 B2 1/2008 Fink et al.
7,351,193 B2 4/2008 Foreman et al.
7,357,770 B1 4/2008 Cutrer et al.
7,402,155 B2 7/2008 Palasis et al.
D575,396 S 8/2008 Wu
7,485,113 B2 2/2009 Varner et al.
7,503,474 B2 3/2009 Hillstead et al.
7,537,593 B2 5/2009 Humayun
7,547,323 B2 6/2009 Lavigne
7,560,460 B2 7/2009 Fotsch et al.

(56) References Cited

U.S. PATENT DOCUMENTS 7,563,222 B2 7/2009 Larsen et al.
7,571,004 B2 8/2009 Roy et al.
7,579,347 B2 8/2009 Bo et al.
7,600,533 B2 10/2009 Tai et al.
7,654,716 B1 2/2010 Bhadri et al.
7,661,676 B2 2/2010 Smith et al.
7,684,868 B2 3/2010 Tai et al.
D615,645 S 5/2010 Brigatti et al.
D616,087 S 5/2010 Brigatti et al.
D616,088 S 5/2010 Brigatti et al.
D616,540 S 5/2010 Brigatti et al.
7,729,739 B2 6/2010 Acar et al.
7,744,520 B2 6/2010 Larsen et al.
7,774,931 B2 8/2010 Tai et al.
7,794,437 B2 9/2010 Humayun et al.
7,803,102 B2 9/2010 Larsen et al.
7,803,103 B2 9/2010 Hillstead et al.
7,810,233 B2 10/2010 Krulevitch et al.
7,827,038 B2 11/2010 Richard et al.
7,831,309 B1 11/2010 Humayun et al.
7,842,686 B2 11/2010 Anderson et al.
7,846,954 B2 12/2010 Zimmermann et al.
7,879,564 B2 2/2011 Brice et al.
7,883,717 B2 2/2011 Varner et al.
7,887,508 B2 2/2011 Meng et al.
7,909,816 B2 3/2011 Buzawa
D642,266 S 7/2011 Marsteller et al.
8,430,804 B2 4/2013 Brigatti et al.
D691,267 S 10/2013 Marsteller et al.
D691,268 S 10/2013 Marsteller et al.
D691,269 S 10/2013 Marsteller et al.
D691,270 S 10/2013 Marsteller et al.
8,597,169 B2 12/2013 Brigatti et al.
8,602,959 B1 12/2013 Park et al.
8,608,632 B1 12/2013 Brigatti et al.
9,056,201 B1 6/2015 Hamilton et al.
D755,385 S 5/2016 Fairbanks et al.
2001/0008950 A1 7/2001 Vitali et al.
2001/0049464 A1 12/2001 Ganz
2002/0002362 A1 1/2002 Humayun et al.
2002/0026174 A1 2/2002 Wallace
2002/0062136 A1 5/2002 Hillstead et al.
2002/0065448 A1 5/2002 Bradshaw et al.
2002/0077687 A1 6/2002 Ahn
2002/0099363 A1 7/2002 Woodward et al.
2002/0115902 A1 8/2002 Dejuan, Jr. et al.
2002/0164061 A1 11/2002 Paik et al.
2002/0198511 A1 12/2002 Varner et al.
2003/0014306 A1 1/2003 Marko
2003/0045900 A1 3/2003 Hahnen et al.
2003/0103945 A1 6/2003 Chen et al.
2003/0153804 A1 8/2003 Tornes et al.
2003/0171722 A1 9/2003 Paques et al.
2003/0184859 A1 10/2003 Liang et al.
2003/0195201 A1 10/2003 Bo et al.
2003/0220324 A1 11/2003 Fotsch et al.
2004/0006067 A1 1/2004 Fotsch et al.
2004/0013855 A1 1/2004 Chen et al.
2004/0039312 A1 2/2004 Hillstead et al.
2004/0053309 A1 3/2004 Holt et al.
2004/0076579 A1 4/2004 Coniglione
2004/0133155 A1 7/2004 Varner et al.
2004/0138515 A1* 7/2004 White .................. A61N 5/1017 600/3
2004/0224777 A1 11/2004 Smith et al.
2004/0243176 A1 12/2004 Hahnen et al.
2005/0059956 A1 3/2005 Varner et al.
2005/0085415 A1 4/2005 Wiesner et al.
2005/0101824 A1 5/2005 Stubbs
2005/0107824 A1 5/2005 Hillstead et al.
2005/0148948 A1 7/2005 Caputa
2005/0149286 A1 7/2005 Acar et al.
2005/0177019 A1 8/2005 DeJuan, Jr. et al.
2005/0203331 A1 9/2005 Szapucki et al.
2005/0227986 A1 10/2005 Bo et al.
2005/0272931 A1 12/2005 Bo et al.
2005/0277802 A1 12/2005 Larsen et al.
2006/0009493 A1 1/2006 Koenig et al.
2006/0030618 A1 2/2006 Bo et al.
2006/0047255 A1 3/2006 Kiehlbauch et al.
2006/0052796 A1 3/2006 Perez et al.
2006/0078087 A1* 4/2006 Forman ................ A61N 5/1001 378/65
2006/0110428 A1 5/2006 deJuan et al.
2006/0111605 A1 5/2006 Larsen et al.
2006/0142629 A1 6/2006 DeJuan, Jr. et al.
2006/0189838 A1 8/2006 Dejuan, Jr. et al.
2006/0223026 A1 10/2006 Kuroiwa et al.
2006/0235877 A1 10/2006 Richard et al.
2006/0257451 A1 11/2006 Varner et al.
2006/0287662 A1 12/2006 Berry et al.
2007/0019790 A1 1/2007 Lewis et al.
2007/0055089 A1 3/2007 Larsen et al.
2007/0118010 A1 5/2007 Hillstead et al.
2007/0179471 A1 8/2007 Christian et al.
2007/0191863 A1 8/2007 De Juan
2007/0219546 A1 9/2007 Mody et al.
2007/0233037 A1 10/2007 Gifford, III et al.
2007/0248545 A1 10/2007 Brice et al.
2007/0265248 A1 11/2007 Fotsch et al.
2007/0265485 A1 11/2007 DeJuan, Jr. et al.
2008/0027266 A1 1/2008 Lebovic et al.
2008/0058704 A1 3/2008 Hee et al.
2008/0089480 A1 4/2008 Gertner
2008/0108933 A1 5/2008 Yu et al.
2008/0154204 A1 6/2008 Varner et al.
2008/0161762 A1 7/2008 Stehr et al.
2008/0172086 A1 7/2008 Hillstead et al.
2008/0200747 A1 8/2008 Wagner et al.
2008/0214887 A1 9/2008 Heanue et al.
2008/0221653 A1 9/2008 Agrawal et al.
2008/0249412 A1 10/2008 Huang et al.
2008/0262512 A1 10/2008 Humayun et al.
2008/0262569 A1 10/2008 Greenberg et al.
2008/0262570 A1 10/2008 Greenberg et al.
2008/0262571 A1 10/2008 Greenberg et al.
2008/0272023 A1 11/2008 McCormick et al.
2008/0281142 A1 11/2008 Lubock et al.
2008/0281254 A1 11/2008 Humayun et al.
2008/0288036 A1 11/2008 Greenberg et al.
2008/0294223 A1 11/2008 Greenberg et al.
2008/0305320 A1 12/2008 Laude et al.
2008/0306611 A1 12/2008 Rowley et al.
2008/0319319 A1 12/2008 Humayun et al.
2009/0016075 A1 1/2009 Bhadri et al.
2009/0030323 A1 1/2009 Fawzi et al.
2009/0036827 A1 2/2009 Cazzini
2009/0069340 A1 3/2009 Balestra et al.
2009/0088784 A1 4/2009 DeBoer et al.
2009/0088843 A1 4/2009 Lu et al.
2009/0101841 A1 4/2009 Boyden et al.
2009/0104960 A1 4/2009 Kelly et al.
2009/0104987 A1 4/2009 Kelly et al.
2009/0112287 A1 4/2009 Greenberg et al.
2009/0131175 A1 5/2009 Kelly et al.
2009/0143124 A1 6/2009 Hughes et al.
2009/0143633 A1 6/2009 Edmundson et al.
2009/0143734 A1 6/2009 Humayun et al.
2009/0146583 A1 6/2009 Bhadri et al.
2009/0149915 A1 6/2009 Greenberg et al.
2009/0177245 A1 7/2009 Ameri et al.
2009/0192493 A1 7/2009 Meng et al.
2009/0227856 A1 9/2009 Russell et al.
2009/0228086 A1 9/2009 Greenberg et al.
2009/0240215 A1 9/2009 Humayun et al.
2009/0264424 A1 10/2009 Bo et al.
2009/0287276 A1 11/2009 Greenberg et al.
2009/0306585 A1 12/2009 Pang et al.
2009/0306594 A1 12/2009 Pang et al.
2009/0306595 A1 12/2009 Shih et al.
2009/0311133 A1 12/2009 Pang et al.
2009/0312742 A1 12/2009 Pang et al.
2010/0004499 A1 1/2010 Brigatti et al.
2010/0004581 A1 1/2010 Brigatti et al.

(56) References Cited

U.S. PATENT DOCUMENTS

| | | | |
|---|---|---|---|
| 2010/0004639 | A1 | 1/2010 | Pang et al. |
| 2010/0025613 | A1 | 2/2010 | Tai et al. |
| 2010/0026957 | A1 | 2/2010 | Tanguay, Jr. et al. |
| 2010/0030010 | A1 | 2/2010 | Vermeere et al. |
| 2010/0076271 | A1 | 3/2010 | Humayun |
| 2010/0100104 | A1 | 4/2010 | Yu et al. |
| 2010/0105454 | A1 | 4/2010 | Weber et al. |
| 2010/0114039 | A1 | 5/2010 | Cazzini |
| 2010/0119696 | A1 | 5/2010 | Yu et al. |
| 2010/0121248 | A1 | 5/2010 | Yu et al. |
| 2010/0121249 | A1 | 5/2010 | Yu et al. |
| 2010/0131075 | A1 | 5/2010 | Ludlow et al. |
| 2010/0157620 | A1 | 6/2010 | Bhadri et al. |
| 2010/0168646 | A1 | 7/2010 | Greenbaum et al. |
| 2010/0174415 | A1 | 7/2010 | Humayun et al. |
| 2010/0197826 | A1 | 8/2010 | Agrawal et al. |
| 2010/0228119 | A1 | 9/2010 | Brennan et al. |
| 2010/0228123 | A1 | 9/2010 | Brennan et al. |
| 2010/0228124 | A1 | 9/2010 | Brennan et al. |
| 2010/0228132 | A1 | 9/2010 | Brennan et al. |
| 2010/0228238 | A1 | 9/2010 | Brennan et al. |
| 2010/0229384 | A1 | 9/2010 | Krulevitch et al. |
| 2010/0238288 | A1 | 9/2010 | Klaerner et al. |
| 2010/0267647 | A1 | 10/2010 | Greenbaum et al. |
| 2010/0268013 | A1 | 10/2010 | Larsen et al. |
| 2010/0294041 | A1 | 11/2010 | Tai et al. |
| 2010/0305550 | A1 | 12/2010 | Meng et al. |
| 2011/0004045 | A1 | 1/2011 | Larsen et al. |
| 2011/0021906 | A1 | 1/2011 | Hillstead et al. |
| 2011/0207987 | A1 | 8/2011 | DiCarlo |
| 2013/0243158 | A1 | 9/2013 | Gertner et al. |
| 2013/0267758 | A1 | 10/2013 | Brigatti et al. |
| 2015/0105601 | A1 | 4/2015 | Finger et al. |
| 2015/0265850 | A1 | 9/2015 | Finger et al. |
| 2016/0375267 | A1 | 12/2016 | Lutz et al. |

FOREIGN PATENT DOCUMENTS

| | | | |
|---|---|---|---|
| AU | 323703 | S | 1/2009 |
| AU | 323704 | S | 1/2009 |
| WO | 200128473 | A1 | 4/2001 |
| WO | 2005016258 | A2 | 2/2005 |
| WO | 2005079294 | A2 | 9/2005 |
| WO | 2007059208 | A2 | 5/2007 |
| WO | 2008076544 | A2 | 6/2008 |
| WO | 2009089288 | A1 | 7/2009 |
| WO | 2011053908 | A1 | 5/2011 |
| WO | 2015105539 | A2 | 7/2015 |

OTHER PUBLICATIONS

Venkatesh et al.; Comparison of the Efficacy and Safety of Different Methods of Posterior Subtenon Injection; Ocular Immunology and Inflammation; Oct. 1, 2007; pp. 217-223; Infoma Healthcare USA, Inc.

Tenon's Capsule; Fundamentals and Principles; p. 39.

Canavan et al.; Sub-Tenon's administration of local anaesthetic: a review of the technique; 2003; pp. 787-793; British Journal of Anaesthesia.

Dafflon et al.; Posterior sub-Tenon's steriod injections for the treatment of posterior ocular inflammation: indications, efficacy and side effects, Graefe's Arch Clin Exp Ophthalmos, 1999, pp. 289-295; Springer-Verlag 1999.

Tanner et al.; Posterior sub-Tenon's triamcinolone injections in the treatment of uveitis; Royal College of Ophthalmologists; 1998; pp. 679-685.

Thach, MD et al.; A Comparison of Retrobulbar versus Sub-Tenon's Corticosteroid Therapy for Cystoid Macular Edema Refractory to Topical Medications; pp. 2003-2008; Ophthalmology vol. 104, No. 12, Dec. 1997.

Hubbard et al.; A New Ocular Brachytherapy System for the Treatment of Exudative AMD; 2005; Invest Ophthalmo Vis Sci 2005; 46; E-Abstract 2425.

Hubbard, III et al.; A Progress Report on the TheraSight Ocular Brachytherapy Safety and Feasibility Study; 2006; Invest Ophthalmol Vis Sci 2006; 47: E-Abstract 2101.

The Collaborative Ocular Melanoma Study Group; Design and Methods of a Clinical Trial for a Rare Condition: The Collaborative Ocular Melanoma Study; COMS Report No. 3; 1993; Controlled Clinical Trials 14: 362-391; Elsevier Science Publishing Co., Inc.

COMS Coordinating Center; Collaborative Ocular Melanoma Study; Manual of Procedures; Jan. 1995; pp. 1-330; The Wilmer Ophthalmological Institute; The Johns Hopkins School of Medicine (*reduced to cover and Table of Contents due to excessive data [330 pages]).

Hubbard et al.; Cadaver Evaluation of a New Ocular Brachytherapy System; Invest Ophthalmol Vis Sci 2004; 45: E-Abstract 5139.

Golden; SubTenon Injection of Gentamicin for Bacterial Infections of the Eye; pp. S271-S277; The Journal of Infectious Diseases; vol. 124, Supplement; Dec. 1971; University of Chicago.

Snyder, MD, PhD et al.; Antibiotic Therapy for Ocular Infection; Conferences and Reviews; pp. 579-584; WJM, Dec. 1994; vol. 161, No. 6; Therapy for Ocular Infection—Snyder and Glasser.

Baum, M.D. et al.; The Evolution of Antibiotic Therapy for Facterial Conjunctivitis and Keratitis: 1970-2000; pp. 659-672; Cornea, vol. 19, No. 5, 2000; Lippincott Williams & Wilkins, Inc., Philadelphia.

Scoper; Review of Third- and Fourth-Generation Fluoroquinolones in Ophthalmology: In-Vitro and In-Vivo Efficacy; Adv Ther. 2008; 25(10): 979-994; Springer Healthcare Communications.

Yilmaz, MD et al.; Severe Fungal Keratitis Treated With Subconjunctival Fluconazole; 2003; pp. 454.e1-454.e7; vol. 140, No. 3; Elsevier Inc.

Yilmaz, MD et al.; Severe Fungal Keratitis Treated With Subconjunctival Fluconazole; Apr. 2006; pp. 783-784; vol. 141, No. 4, Correspondence; American Journal of Ophthalmology.

Ikewaki et al.; Peribulbar fungal abscess and endophthalmitis following posterior subtenon injection of triamcinolone acetonide; Diagnolis/Therapy in Ophthalmology; 2008; pp. 102-104; Acta Ophthalmologica; The Authors, Journal compilation, Acta Ophthalmol.

Nayak et al.; Acute orbital abscess complicating deep posterior subtenon triamcinolone injection; Indian Journal of Ophthalmology; vol. 56, No. 3; May-Jun. 2008; downloaded from http://www.ijo.in on Monday, Nov. 2, 2009.

Kusaka et al.; Orbital infection following posterior subtenon triamcinolone injection; 2207; pp. 692-693; Acta Ophthalmologica Scandinavica.

Walker et al.; Conservative management of refractory steroid-induced glaucoma following anterior subtenon steroid injection; 2007; Letters to the Editor; pp. 197-198; The Authors, Journal compilation, Royal Australian and New Zealand College of Ophthalmologists.

Au et al.; Localised abscess following an injection of subtenon triamcinolone acitonide; Correspondence; Eye (2007) 21, 627-674, doi:10.1038/sj.eye.6702671; published online Dec. 15, 2006.

Venkatesh MD, et al.; Posterior subtenon injection of corticosteroids using polytetrafiuoroethylene (PEFE) intravenous cannula; Clinical and Experimental Ophthalmology (2002) 30, 55-57; All India Institute of Medical Sciences Campus, India.

Sou-Tung Chiu-Tsao, Ph.D., Episcleral Eye Plaques for Treatment of Intraocular Malignancies and Benign Diseases; Chapter 34; pp. 673-705.

Sou-Tung Chiu-Tsao, Ph.D., Pterygium Brachytherapy Physics; Chapter 35; pp. 707-717.

Nath, Ravinder, Ph.D. et al.; Brachytherapy Physics Second Edition; Medical Physics Monograph No. 31; 1013 pages; Medical Physics Publishing; Madison, Wisconsin, USA; 2005.

Jaakkola, Aino; Heikkonen, Jorma; Tarkkanen, Ahti and Immonen, Ilkka; Visual function after strontium-90 plaque irradiation in patients with age-related subfoveal choroidal neovascularization; Acta Opthalmologica Scandinavica 1999; 77; pp. 57-61.

Hokkanen, J.; Heikkonen, J.; Holmberg, P.; Theoretical calculations of dose distributions for beta-ray eye applicators; Med. Phys. 24 (2); Feb. 1997pp. 211-213.

Jaakkola, Aino; Heikkonen, Jorma; Tommila, Petri; Laatikainen, Leila; Immonen, Ilkka; Strontium plaque irradiation of subfoveal neovascular membranes in age-related macular degeneration; Graefe's Arch Clin Exp Ophthalmol (1998); 236; pp. 24-30.

(56) References Cited

OTHER PUBLICATIONS

J. M. Capping; Radiation scleral necrosis simulating early scleromalacia perforans; Brit. J. Ophthal.; 1973; 57; pp. 425-428.
JC Wen et al; Ocular complications following I-125 brachytherapy for choroidal melanoma; Eye; 2009; 23; 1254-1268.
Messmer E et al.; Histopathologic findings in eyes treated with a ruthenium plaque for uveal melanoma; Graefes Arch Clin Exp Ophthalmol.; 1992; 230 (4): 391-6.

* cited by examiner

METHODS AND DEVICES FOR MINIM ALLY-INVASIVE DELIVERY OF RADIATION TO THE EYE

CROSS REFERENCE

This application is a divisional of U.S. patent application Ser. No. 14/486,401, filed Sep. 15, 2014, which is a non-provisional of and claims priority to U.S. Provisional Patent Application No. 61/877,765, filed Sep. 13, 2013, the specification(s) of which is/are incorporated herein in their entirety by reference.

U.S. patent application Ser. No. 14/486,401 also claims priority to U.S. patent application Ser. No. 13/872,941, filed Apr. 29, 2013, which is a division of U.S. patent application Ser. No. 12/350,079, filed Jan. 7, 2009, which is a non-provisional of U.S. Provisional Application No. 61/010,322, filed Jan. 7, 2008, U.S. Provisional Application No. 61/033,238, filed Mar. 3, 2008, U.S. Provisional Application No. 61/035,371, filed Mar. 10, 2008, and U.S. Provisional Application No. 61/047,693, filed Apr. 24, 2008, the specification(s) of which is/are incorporated herein in their entirety by reference.

U.S. patent application Ser. No. 14/486,401 also claims priority to U.S. patent application Ser. No. 13/953,528, filed Jul. 29, 2013, which is a non-provisional of U.S. Provisional Application No. 61/676,783, filed Jul. 27, 2012, the specification(s) of which is/are incorporated herein in their entirety by reference.

U.S. patent application Ser. No. 14/486,401 also claims priority to U.S. patent application Ser. No. 14/011,516, filed Aug. 27, 2013, which claims priority to U.S. patent application Ser. No. 13/742,823, filed Jan. 16, 2013, which is a continuation of U.S. patent application Ser. No. 12/497,644, filed Jul. 3, 2009, which is a continuation-in-part of U.S. patent application Ser. No. 12/350,079, filed Jan. 7, 2009, which is a non-provisional of U.S. Provisional Application No. 61/010,322, filed Jan. 7, 2008, U.S. Provisional Application No. 61/033,238, filed Mar. 3, 2008, U.S. Provisional Application No. 61/035,371, filed Mar. 10, 2008, and U.S. Provisional Application No. 61/047,693, filed Apr. 24, 2008, the specification(s) of which is/are incorporated herein in their entirety by reference. Application Ser. No. 14/011,516 also claims priority to U.S. patent application Ser. No. 13/111,780, filed May 19, 2011, which is a non-provisional of U.S. Provisional Application No. 61/347,226, filed May 21, 2010; and a continuation-in-part of U.S. patent application Ser. No. 12/497,644, filed Jul. 3, 2009, which is a continuation-in-part of U.S. patent application Ser. No. 12/350,079, filed Jan. 7, 2009, which is a non-provisional of U.S. Provisional Application No. 61/010,322, filed Jan. 7, 2008, U.S. Provisional Application No. 61/033,238, filed Mar. 3, 2008, U.S. Provisional Application No. 61/035,371, filed Mar. 10, 2008, and U.S. Provisional Application No. 61/047,693, filed Apr. 24, 2008, the specification(s) of which is/are incorporated herein in their entirety by reference. Application Ser. No. 14/011,516 also claims priority to U.S. patent application Ser. No. 12/917,044, filed Nov. 1, 2010, which is a non-provisional of U.S. Provisional Application Ser. No. 61/257,232, filed Nov. 2, 2009 and U.S. Provisional Application No. 61/376,115, filed Aug. 23, 2010, the specification(s) of which is/are incorporated herein in their entirety by reference. Application Ser. No. 14/011,516 also claims priority to U.S. patent application Ser. No. 13/111,765, filed May 19, 2011, which is a non-provisional of U.S. Provisional Application No. 61/347,233, filed May 21, 2010, the specification(s) of which is/are incorporated herein in their entirety by reference. Application Ser. No. 14/011,516 also claims priority to U.S. patent application Ser. No. 13/953,528, filed Jul. 29, 2013, which is a non-provisional of U.S. Provisional Application No. 61/676,783, filed Jul. 27, 2012, the specification(s) of which is/are incorporated herein in their entirety by reference.

FIELD OF THE INVENTION

The present invention relates to methods and devices for introducing radiation to the eye, e.g., the posterior portion of the eye, for treating and/or managing eye conditions including but not limited to macular degeneration.

BACKGROUND OF THE INVENTION

The present invention features methods and devices for minimally-invasive delivery of radiation to the eye, e.g., the posterior portion of the eye. For example, the present invention features cannula systems and afterloading systems (e.g., remote afterloading systems) for introducing emanating sources (e.g., active material, radionuclide brachytherapy sources) to the cannula systems for irradiating targets (e.g., targets of the eye). The emanating source may be, for example, introduced into the cannula system via an afterloading system following cannula system insertion and positioning.

Presently, workers in the field of radiation therapy believe that a barrel-shaped or disk-shaped radiation projection at the surface of the radiation source is the proper radiation profile for treating neovascular lesion of wet AMD. We have surprisingly discovered that radiation flux with an attenuation zone, e.g., a centrally disposed attenuation zone, provides for more effective treatment of neovascular lesion of wet AMD from the posterior episcleral surface.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DESCRIPTION OF PREFERRED EMBODIMENTS

Figure 1:
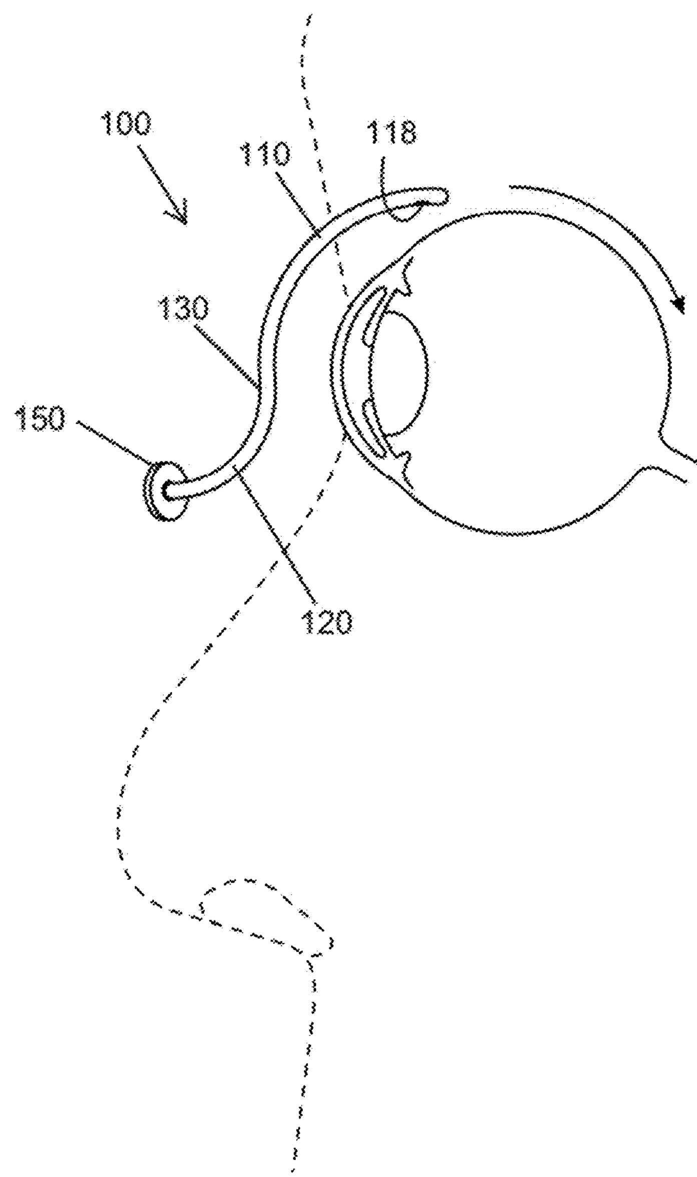
FIG. 1 shows an in-use view of a cannula system of the present invention.
Figure 2:
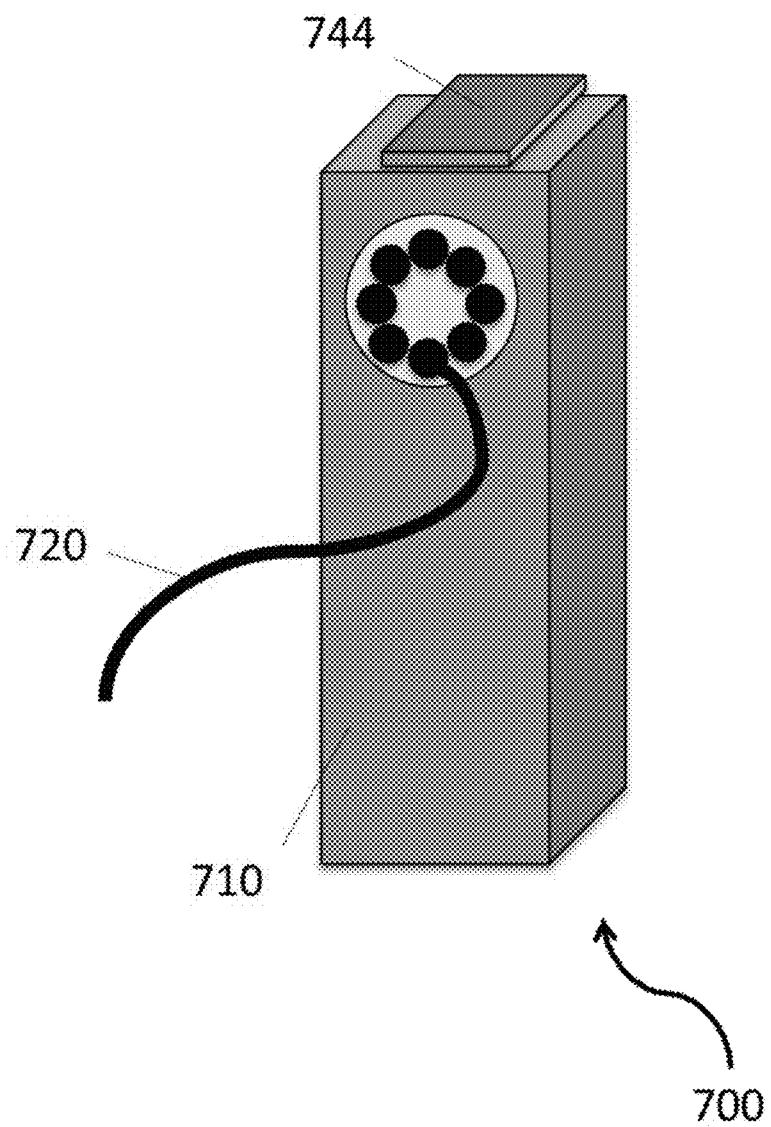
FIG. 2 shows a schematic view of an afterloading system of the present invention. Afterloading systems are well known to one of ordinary skill in the art. The present invention is not limited to the afterloading systems described herein.
Figure 3A:
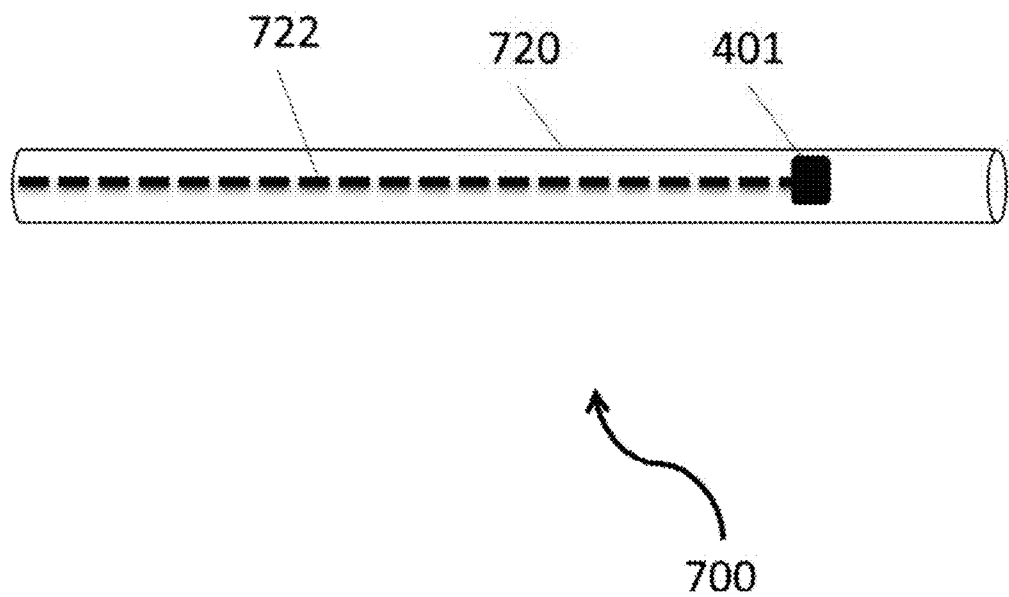
FIG. 3A shows the advancing means and emanating source within the guide tube.
Figure 3B:
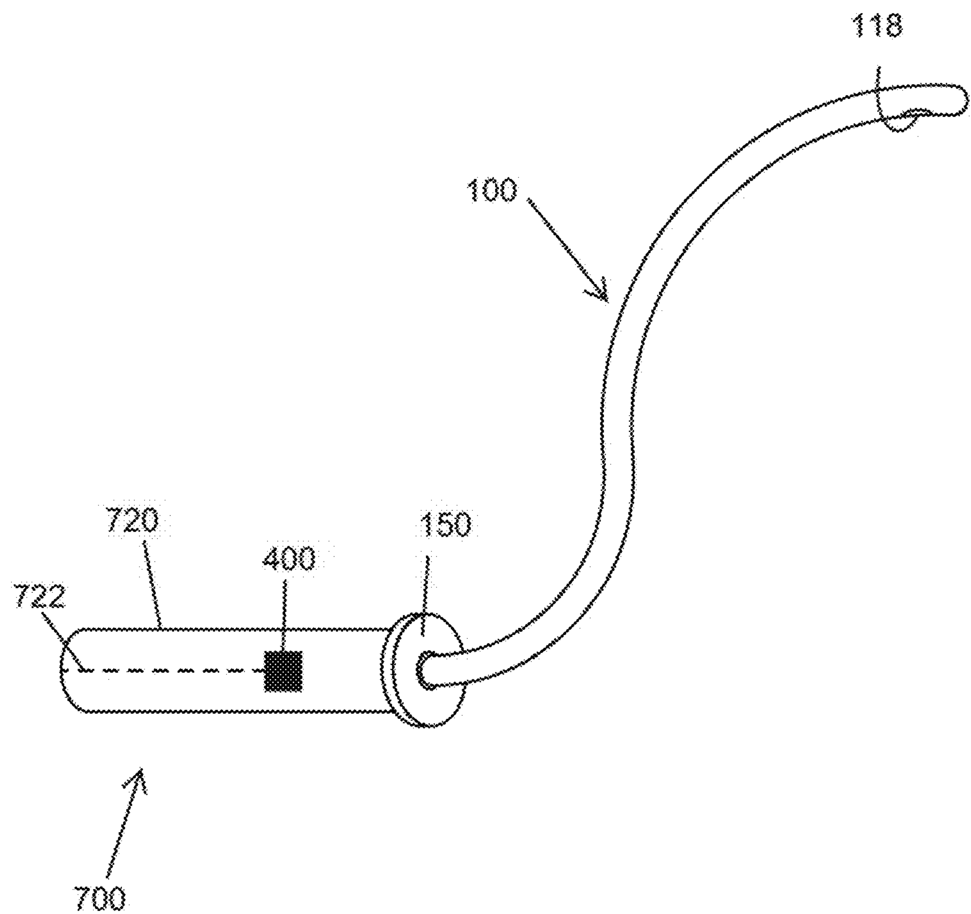
FIG. 3B shows the guide tube connecting to the cannula system.

Following is a list of elements corresponding to a particular element referred to herein:

100 cannula system
110 distal portion of cannula system
112 tip/distal end of distal portion of cannula system
113 center
114 light aperture in tip of distal portion of cannula system
116 light source plug compartment
118 treatment position
120 proximal portion of cannula system
130 inflection point of cannula system
140 handle
150 connector (optional)
160 channel
401 emanating source
401*a* annulus-shaped emanating source
401*b* disc-shaped emanating source
402 jacket
404 radiation shaper
406 radiation emission shape
407 annulus-shaped radiation emission shape
410 attenuation zone
412 outer edge of attenuation zone
414 hole
416 indentation
450 radiation flux
600 light source assembly
610 light source emitter component
612 light pipe (e.g., fiber optic cable or other light guide)
613 prism
614 light source plug
616 tip of light source plug
617 locking mechanism
618 groove
700 afterloading system
710 vault
720 guide tube
722 advancing means (e.g., guide wire)
730 source-drive mechanism
732 motor
740 computer (e.g., microprocessor)
744 control console Referring now to FIG. 1-12, the present invention features methods and devices for minimally-invasive delivery of radiation to the eye, e.g., the posterior portion of the eye. For example, the present invention features afterloading systems (700) (e.g., remote afterloading systems) for introducing an emanating source (401) to a cannula system (100). The cannula system (100) may be adapted for insertion into a potential space between the sclera and the Tenon's capsule of the eye of a patient.

The present methods and devices may be effective for treating and/or managing a condition (e.g., an eye condition). For example, the present methods and devices may be used to treat and/or manage wet (neovascular) age-related macular degeneration. The present methods are not limited to treating and/or managing wet (neovascular) age-related macular degeneration. For example, the present methods may also be used to apply superficial radiation to benign or malignant ocular growths (e.g., choroidal hemangioma, choroidal melanoma, retinoblastoma) and or to treat and/or manage conditions including macular degeneration, abnormal cell proliferation, choroidal neovascularization, retinopathy (e.g., diabetic retinopathy, vitreoretinopathy), macular edema, and tumors.

In some embodiments, the present invention features an emanating source system, the emanating source system comprising an emanating source (401) whereby the radiation emission shape (406) is in the shape of an annulus or partial annulus. In some embodiments, the emanating source (401) is in the shape of an annulus or a partial annulus. In some embodiments, the emanating source (401) comprises a plurality of discrete seeds that have a cumulative radiation emission shape (406) of an annulus or partial annulus. In some embodiments, the emanating source (401) comprises any arrangement of sources that yield a radiation emission shape (406) in the shape of an annulus or partial annulus. In some embodiments, the emanating source (401) comprises a radiation shaper (404); the radiation shaper (404) shapes the radiation emitted from the emanating source (401) into a radiation emission shape (406) in the shape of an annulus or partial annulus. In some embodiments, the emanating source (401) unit is housed in a jacket (402). In some embodiments, the emanating source (401) unit is attached to a cannula, a cannula system (100), a rod, or a stick.

In some embodiments, the present invention features a method of irradiating a target of an eye in a patient, said method comprising exposing a target of an eye with an emanating source (401) that has an radiation emission shape (406) of an annulus. In some embodiments, the target comprises a neovascular lesion of wet AMD. In some embodiments, the emanating source (401) is adjacent to the retrobulbar episcleral surface.

In some embodiments, the present invention features a method of irradiating a target of an eye in a patient, said method comprising inserting a cannula system into a potential space between a sclera and a Tenon's capsule of the eye of the patient; placing a distal portion (110) of the cannula system (100) on or near the sclera and positioning a treatment position (118) of a tip (112) of the distal portion (110) of the cannula system (100) near the target; advancing an emanating source (401) through the cannula system (100) to the treatment position (118) in the distal portion (110) of the cannula system (100), wherein the radiation emission shape (406) of the emanating source (401) creates a radiation emission shape (406) of an annulus; exposing the target to the emanating source (401); retracting the emanating source (401); and removing the cannula system (100). In some embodiments, the emanating source (401) comprises a single unit or a plurality of discrete units that are positioned either simultaneously or by sequential positioning. In some embodiments, the cannula system comprises a cannula system (100).

In some embodiments, the present invention features a method of irradiating a target of an eye in a patient, said method comprising advancing an emanating source (401) through a cannula system (100) to a treatment position (118) in a distal portion (110) of a cannula system (100); inserting the cannula system (100) into a potential space between a sclera and a Tenon's capsule of the eye of the patient; placing a distal portion (110) of the cannula system (100) on or near the sclera and positioning the treatment position (118) of the cannula system (100) near the target; exposing the target to the emanating source (401); and removing the cannula system (100). In some embodiments, the emanating source (401) comprises a single unit or a plurality of discrete units that are positioned either simultaneously or by sequential positioning. In some embodiments, the cannula system comprises a cannula system (100).

In some embodiments, the present invention features a brachytherapy system comprising a cannula system (100) for insertion into a potential space between a sclera and a Tenon's capsule of an eye of a patient. In some embodiments, the cannula system (100) comprises a distal portion (110) with a tip (112), a channel (160) extends through the cannula system (100) to the tip (112), the channel (160) comprises at least one treatment position (118) in the tip (112) for an emanating source (401).

In some embodiments, the cannula system (100) comprises two channels (160). In some embodiments, the cannula system (100) comprises three channels (160). In some embodiments, the cannula system (100) comprises four channels (160). In some embodiments, the cannula system (100) comprises more than four channels (160).

In some embodiments, the channel (160) comprises two treatment positions (118). In some embodiments, the channel (160) comprises three treatment positions (118). In some embodiments, the channel (160) comprises four treatment positions (118). In some embodiments, the channel (160) comprises five treatment positions (118). In some embodiments, the channel (160) comprises six treatment positions (118). In some embodiments, the channel (160) comprises more than six treatment positions (118).

In some embodiments, the emanating source (401) is directed through one or more channels (160) to one or more treatment positions (118) that in summation deliver a dose to the target approximating that emanating from an annulus. In some embodiments, the tip (112) of the cannula system (100) is disk-shaped. In some embodiments, the emanating source (401) is horseshoe shaped. In some embodiments, the emanating source (401) is an annulus or a partial annulus. In some embodiments, the emanating source (401) is linear. In some embodiments, the emanating source (401) comprises one or more discrete seeds.

In some embodiments, the discrete seeds are arranged in an annulus or partial annulus configuration. In some embodiments, the emanating source (401) comprises a continuous ring or a portion of a ring. In some embodiments, the brachytherapy system further comprises a light source assembly (600).

In some embodiments, the light source assembly (600) comprises a fiber optic cable or light pipe (612) operatively connected to an external light source. a light source plug (614) is disposed on an end of the fiber optic cable or light pipe (612), a light source emitter component (610) is incorporated into the light source plug (614), the light source plug (610) and light source emitter component (610) are adapted to engage a light source plug compartment (116) disposed in the tip (112) of the distal portion (110) of the cannula system (100). In some embodiments, the light source plug (614) and light source emitter component (610) engage a light aperture (114) disposed on a bottom surface of the tip (112) of the cannula system (100). In some embodiments, a prism is disposed at the end of the fiber optic cable or light pipe (612). In some embodiments, the light source plug (614) is secured in the light source plug compartment (116) via a locking mechanism. In some embodiments, a groove (618) is disposed in the cannula system (100) adapted to engage the fiber optic cable or light pipe (612).

In some embodiments, the brachytherapy system further comprises an afterloading system (700) for delivering the emanating sources (401) (400) to the treatment position(s) (118). In some embodiments, the afterloading system (700) comprises a guide tube (720) for each channel (160) in the cannula system (100). In some embodiments, the afterloading system (700) comprises: a vault (710) for storage of an emanating source (401), wherein the emanating source (401) is attached to an advancing means (722); a guide tube (720) extending from the vault (710), the guide tube (720) is removably attachable to the cannula system (100); and a source-drive mechanism (730) operatively connected to the advancing means (722), wherein the source-drive mechanism (730) advances the emanating source (401) through the guide tube (720) to the treatment position (118) in the cannula system (100). In some embodiments, the emanating source (401) provides a dose rate of between about 1 to 10 Gy/min to a target.

In some embodiments, the cannula system (100) comprises a proximal portion (120) connected to the distal portion (110) by an inflection point (130), the distal portion (110) has a radius of curvature between about 9 to 15 mm and an arc length between about 25 to 35 mm and the proximal portion (120) has a radius of curvature between about an inner cross-sectional radius of the cannula system (100) and about 1 meter.

In some embodiments, the present invention features a method of irradiating a target of an eye in a patient, said method comprising inserting a cannula system (100) into a potential space between a sclera and a Tenon's capsule of the eye of the patient; placing a distal portion (110) of the cannula system (100) on or near the sclera and positioning a treatment position (118) of a tip (112) of the distal portion (110) of the cannula system (100) near the target; advancing an emanating source (401) through the cannula system (100) to the treatment position (118) in the distal portion (110) of the cannula system (100); exposing the target to the emanating source (401); retracting the emanating source (401); and removing the cannula system (100).

In some embodiments, the emanating source (401) travels to each treatment position (118) sequentially. In some embodiments, the emanating source (401) travels to selected treatment positions (118) sequentially. In some embodiments, the emanating source (401) travels to each treatment positions (118) in a selected order. In some embodiments, the emanating source (401) travels to selected treatment positions (118) in a selected order. In some embodiments, the cannula system (100) is operatively connected to an afterloading system (700). In some embodiments, the afterloading system (700) is operatively connected to the cannula system (100) after the cannula system (100) is positioned in between the Tenon's capsule and sclera. In some embodiments, the afterloading system (700) is operatively connected to the cannula system (100) before the cannula system (100) is positioned in between the Tenon's capsule and sclera. In some embodiments, both (a) the afterloading system (700) is operatively connected to the cannula system (100) and (b) the emanating source (401) is advanced before the cannula system (100) is positioned in between the Tenon's capsule and sclera.

Cannula System

As shown in FIG. 1, the cannula system (100) comprises a distal portion (110) and a proximal portion (120) connected by an inflection point (130). The distal portion (110) is generally for placement around a portion of the globe of the eye. In some embodiments, the distal portion (110) has a radius of curvature between about 9 to 15 mm and an arc length between about 25 to 35 mm. In some embodiments, the proximal portion (120) has a radius of curvature between about an inner cross-sectional radius of the cannula system (100) and about 1 meter. The cannula system (100), or a portion thereof, may be flexible, fixed-shape, or a combination thereof. The cannula system (100) is not limited to the aforementioned dimensions and configurations.

The cannula system (100) may be operatively connected to an afterloading system (700) having an emanating source (401). The afterloading system (700) can deliver the emanating source (401) to the cannula system (100) (e.g., to a treatment position (118) of the cannula system (100), to at least one treatment position, to one or more treatment positions, etc.). For example, the afterloading system (700) can direct the emanating source (401) to a position within the cannula system (100) (e.g., a treatment position (118), at least one treatment position, one or more treatment positions, etc.) such that the emanating source (401) is over a target. The emanating source (401) can then irradiate the target for a length of time desired. The afterloading system (700) may also function to remove the emanating source (401) from the position within the cannula system (e.g., the treatment position(s) (118)) and from the cannula system (100) altogether. For example, the afterloading system (700) may retract the emanating source (401) to its starting position outside of the cannula system (100).

The cannula system (100) may comprise one or more treatment positions (118) and/or channels (160) (as described below). In some embodiments, an afterloading system (700) may function to deliver one or more emanating sources (401) to one or more treatment positions (118) in one or more channels (160) of the cannula system (100).

In some embodiments, the cannula system (100) is inserted, e.g., into the potential space between the sclera and the Tenon's capsule, and is positioned appropriately prior to attachment of the afterloading system (700). For example, the distal portion (110) of the cannula system is placed on or near the sclera and the treatment position(s) (118) of the cannula system (100) (e.g., in the distal portion (110)) or treatment position(s), is positioned near the target. Following placement and positioning of the cannula system, the afterloading system (700) may be connected to the cannula system. In some embodiments, the cannula system (100) and the afterloading system (700) are connected prior to insertion of the cannula system (100), e.g., into the potential space between the sclera and the Tenon's capsule. In some embodiments, the cannula system (100) and the afterloading system (700) are connected prior to insertion of the cannula system (100), e.g., into the potential space between the sclera and the Tenon's capsule, and the emanating source (401) advanced to the treatment position prior to the cannula system being introduced to the sub-tenon's space.

Figure 5:
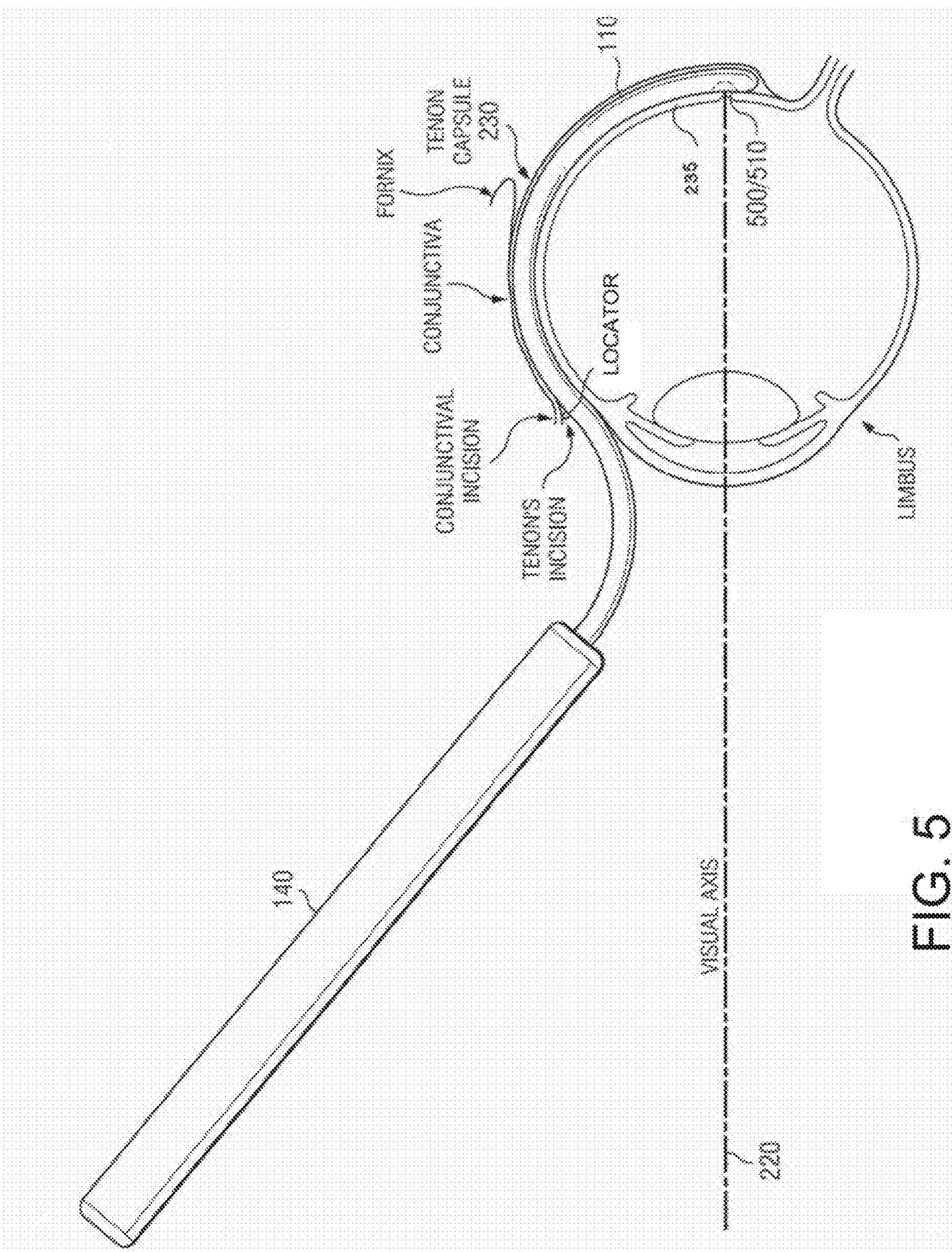
FIG. 5 shows the insertion of a fixed shape cannula according to the present invention. The tip of the cannula system is positioned at the back of the eye. Part (220) refers to the visual axis of the user; Part (230) refers to the Tenon's capsule; Part (235) refers to the sclera; Part (500) refers to an orifice; Part (510) refers to a window. The present invention is not limited to the configuration and parts of the cannula shown in FIG. 5.

In some embodiments, the cannula system (100) is connected to a handle and/or shielding system (e.g., radiation shielding PIG). For example, the cannula system (100) in FIG. 5 is attached to a handle (140).

Afterloading System

The afterloading system (700) may allow for accurate placement of the emanating source (401), e.g., at the treatment position(s) (118) within the cannula system (100). Afterloading systems (700) are well known to one of ordinary skill in the art and any appropriate afterloading system (700) may be utilized. For example, in some embodiments, the afterloading system (700) comprises a vault (710) for temporary housing of the emanating source (401). The emanating source (401) may be attached to an advancing means (722) (e.g., a guide wire). In some embodiments, the emanating source (401) may be incorporated into the advancing mean (722) (e.g., guide wire). The advancing means (722) (e.g., guide wire) may be constructed from any appropriate material including but not limited to nitinol and stainless steel. A guide tube (720) extends from the vault (710) and is connected to the cannula system (100). In some embodiments, the guide tube (720) connects, e.g., removably connects, to the cannula system (100) via a connector (150). In some embodiments, the connector (150) is disposed on the cannula system (100), e.g., on the proximal portion (120) of the cannula system (100). The advancing means (722) directs the emanating source (401) through the guide tube (720), e.g., the advancing means (722) may be disposed in at least a portion of the guide tube (720).

The afterloading system (700) comprises a source-drive mechanism (730) operatively connected to the advancing means (722) (e.g., guide wire). The source-drive mechanism (730) functions to advance the advancing means (722) (e.g., guide wire) and emanating source (401) through the guide tube (720) to the treatment position(s) (118) in the cannula system (100). In some embodiments, the source-drive mechanism (730) comprises a motor (732). In some embodiments, the motor (732) comprises drive rollers or belts.

In some embodiments, the afterloading system (700) comprises a computer (740) (e.g., a microprocessor) or other controller (e.g., an analog or a mechanical control system). The motor (732) and/or source-drive mechanism (730) may be operatively connected to the computer (740) or other controller. In some embodiments, the computer (740) or other controller is operatively connected to a control console (744). The control console (744) allows for manipulation of the computer (740) or other controller. For example, the control console (744) may allow for programming of the afterloading system (700), e.g., dwell time of the emanating source (401) in the treatment position(s) (118), speed of delivery of the emanating source (401), etc. In some embodiments, the afterloading system (700) moves the emanating source (401) from the vault (710) to the treatment position(s) (118) at a rate of between about 0.01 m/s (1 cm/s) to about 4 m/s. In some embodiments, the afterloading system (700) moves the emanating source (401) from the vault (710) to the treatment position(s) (118) at a rate of about 2 m/s.

The afterloading system (700) may measure various parameters of the treatment. For example, in some embodiments, the afterloading system (700) measures dwell time of the emanating source (401) in the treatment position(s) (118).

In some embodiments, the guide tube (720) is constructed from a material that provides some shielding from the radiation emitted from the emanating source (401) as it travels through the guide tube (720)

In some embodiments, the afterloading system (700) further comprises a selector, for example for treatments that require multiple applicators or cannula systems (100). The selector may provide multiple channels, e.g., between 1 to 10 channels, between 2 to 10 channels, between 2 to 20 channels, between 16 to 24 channels, between 18 to 24 channels, more than 24 channels, etc. The selector may facilitate the movement (e.g., entry, transfer) of the emanating source (401) through multiple applicators (e.g., cannula systems (100)), if necessary.

Emanating Source

The methods and devices of the present invention may feature any appropriate emanating source (401). In some embodiments, the emanating source (401) is a high-dose-rate (HDR) source. In some embodiments, the emanating source (401) is a low-dose-rate (LDR) source. In some embodiments, the emanating source (401) is a pulsed-dose-rate (PDR) source. In some embodiments, the emanating source (401), e.g., HDR source, delivers a dose rate greater than 100 cGy per minute for a length of time. However the present invention is not limited to a HDR source that delivers a dose rate greater than 100 cGy per minute. In some embodiments, the emanating source (401) provides a dose rate of between about 2 to 10 Gy/min to the target. In some embodiments, the emanating source (401) provides a dose rate of between about 1 to 10 Gy/min to the target. In some embodiments, the emanating source (401) provides a dose rate of between about 2 to 6 Gy/min to the target. In some embodiments, the emanating source (401) provides a dose rate of about 4.4 Gy/min to the target. In some embodiments, a LDR source provides a dose rate of less than about 2 Gy/hour. In some embodiments, a medium-dose-rate (MDR) source provides a dose rate of between about 2 to 12 Gy/hour. In some embodiments, a HDR source provides a dose rate of greater than about 12 Gy/hour.

In some embodiments, the emanating source (401) provides a dose rate of greater than about 10 Gy/min. In some embodiments, the emanating source (401) provides a dose rate of greater than about 11 Gy/min to the target. In some embodiments, the emanating source (401) provides a dose rate of greater than about 12 Gy/min to the target. In some embodiments, the emanating source (401) provides a dose rate of greater than about 13 Gy/min to the target. In some embodiments, the emanating source (401) provides a dose rate of greater than about 14 Gy/min to the target. In some embodiments, the emanating source (401) provides a dose rate of greater than about 15 Gy/min to the target. In some embodiments, the emanating source (401) provides a dose rate between about 10 to 15 Gy/min. In some embodiments, the emanating source (401) provides a dose rate between about 15 to 20 Gy/min. In some embodiments, the emanating source (401) provides a dose rate between about 20 to 30 Gy/min. In some embodiments, the emanating source (401) provides a dose rate between about 30 to 40 Gy/min. In some embodiments, the emanating source (401) provides a dose rate between about 40 to 50 Gy/min. In some embodiments, the emanating source (401) provides a dose rate between about 50 to 60 Gy/min. In some embodiments, the emanating source (401) provides a dose rate between about 60 to 70 Gy/min. In some embodiments, the emanating source (401) provides a dose rate between about 70 to 80 Gy/min. In some embodiments, the emanating source (401) provides a dose rate between about 80 to 90 Gy/min. In some embodiments, the emanating source (401) provides a dose rate between about 90 to 100 Gy/min. In some embodiments, the emanating source (401) provides a dose rate of greater than 100 Gy/min.

In some embodiments, the emanating source (401) provides a dose rate between about 15 to 20 Gy/min to the target. In some embodiments, the emanating source (401) provides a dose rate between about 20 to 25 Gy/min to the target. In some embodiments, the emanating source (401) provides a dose rate between about 25 to 30 Gy/min to the target. In some embodiments, the emanating source (401) provides a dose rate between about 30 to 35 Gy/min to the target. In some embodiments, the emanating source (401) provides a dose rate between about 35 to 40 Gy/min to the target. In some embodiments, the emanating source (401) provides a dose rate between about 40 to 50 Gy/min to the target. In some embodiments, the emanating source (401) provides a dose rate between about 50 to 60 Gy/min to the target. In some embodiments, the emanating source (401) provides a dose rate between about 60 to 70 Gy/min to the target. In some embodiments, the emanating source (401) provides a dose rate between about 70 to 80 Gy/min to the target. In some embodiments, the emanating source (401) provides a dose rate between about 80 to 90 Gy/min to the target. In some embodiments, the emanating source (401) provides a dose rate between about 90 to 100 Gy/min to the target. In some embodiments, the emanating source (401) provides a dose rate greater than about 100 Gy/min to the target.

Multi-Channel-Multi-Treatment Position Cannula System

Figure 4A:
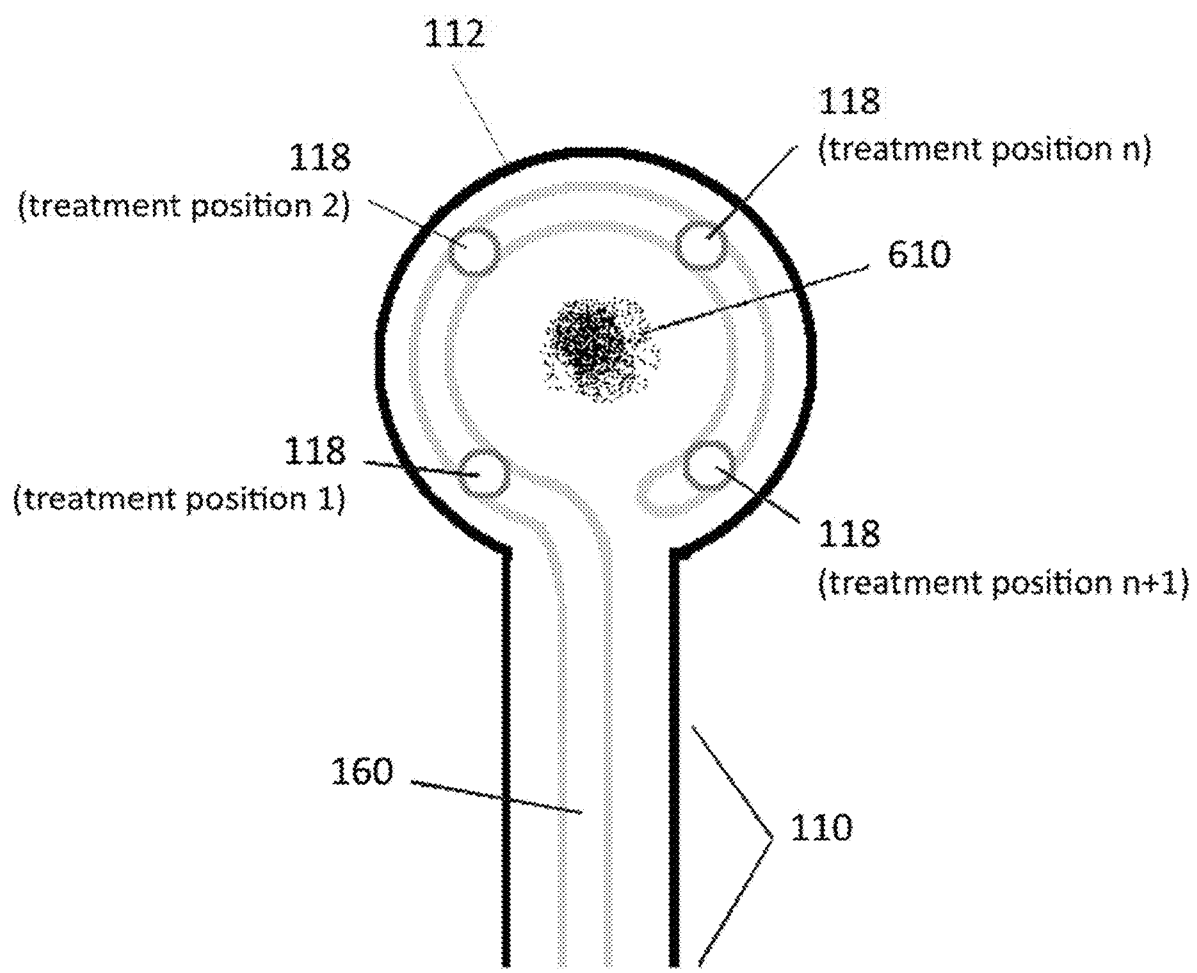
FIG. 4A shows a detailed view of the distal portion of a cannula system comprising a single channel through which an emanating source can travel. The cannula system comprises a plurality of treatment positions within the channel (e.g., treatment position 1, treatment position 2, treatment position n, treatment position n+1, etc.).

The cannula system (100) may comprise multiple channels (160) through which an emanating source (401) can travel to the tip/distal end (112) of the distal portion (110) of the cannula system (100) and/or multiple treatment positions (118) for the emanating sources (401) within the tip (112). For example, FIG. 4A shows a cannula system (100) comprising a single channel (160) through which an emanating source (401) can travel through and within the tip (112) of the cannula system (100). The cannula system (100) comprises a plurality of treatment positions (118) within the channel (160) (e.g., treatment positions positioned in the tip (112) of the cannula system (100)): treatment position 1, treatment position 2, treatment position n, and treatment position n+1.

As shown in FIG. 5B of the parent provisional application, a cannula system (100) comprises a plurality of channels (160) (e.g., channel 1, channel 2, channel n, channel n+1) through which an emanating source (401) can travel. The cannula system (100) comprises a plurality of treatment positions (118) (in FIG. 5B each channel (160) has a single treatment position (118), however in some embodiments each channel (160) may have multiple treatment positions (118)), wherein an emanating source (401) in channel 1 is directed to treatment position 1, an emanating source (401) in channel 2 is directed to treatment position 2, an emanating source (401) in channel n is directed to treatment position n, and an emanating source (401) in channel n+1 is directed to treatment position n+1.

Figure 4B:
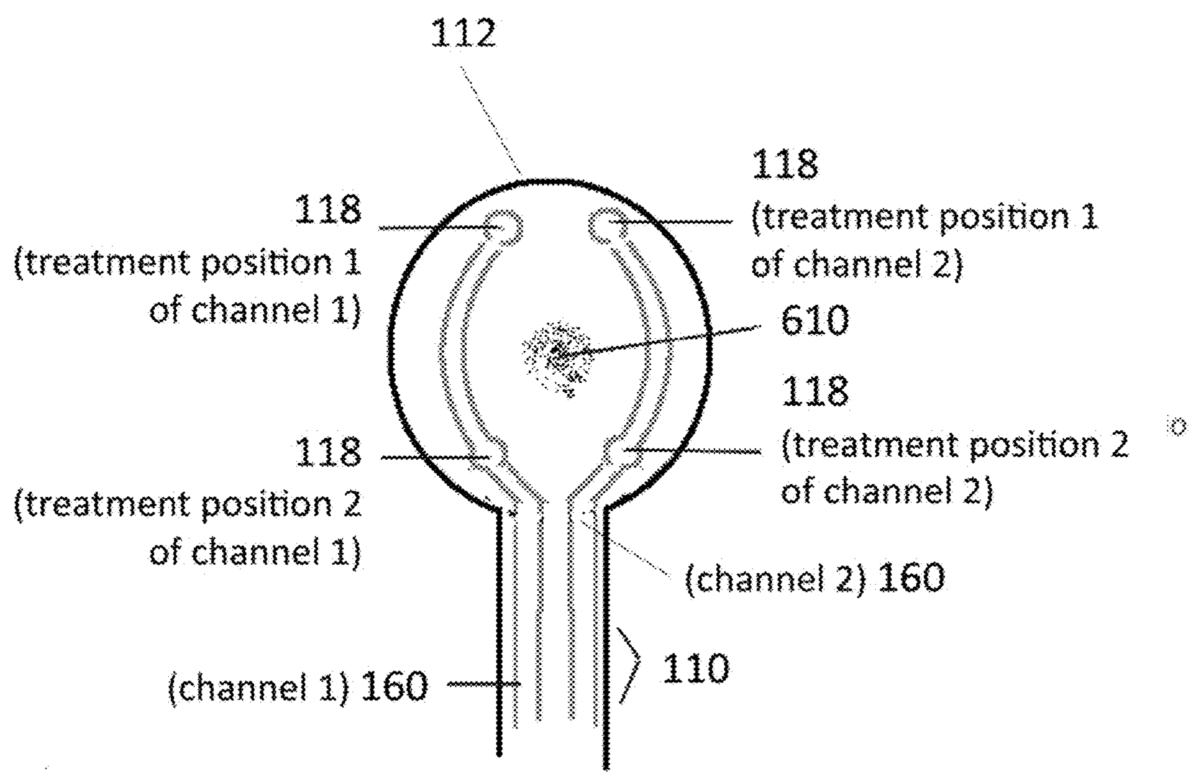
FIG. 4B shows a detailed view of the distal portion of a cannula system comprising more than one channel (e.g., 2 channels) through which an emanating source can travel, wherein the channels each comprise more than one treatment position (e.g., treatment position 1, treatment position 2) for the emanating source.

FIG. 4B shows an example of a cannula system comprising more than one channel (e.g., 2 channels) through which an emanating source (401) can travel, wherein the channels each comprise more than one treatment position (e.g., treatment position 1, treatment position 2) for the emanating source (401). The system of the present invention is not limited to the number of treatment positions, channels, or configuration or arrangements shown herein.

The present invention is not limited to the number of treatment positions, channels, or configuration or arrangements of such treatment positions and channels shown herein. For example, in some embodiments, the system (100) comprises one treatment position, two treatment positions, three treatment positions, four treatment positions, five treatment positions, six treatment positions, seven treatment positions, eight treatment positions, nine treatment positions. 10 treatment positions, 11 treatment positions, 12 treatment positions, 13 treatment positions, 14 treatment positions, 15 treatment positions, 16 treatment positions, 17 treatment positions, 18 treatment positions, 19 treatment positions, 20 treatment positions, or more than 20 treatment positions. In some embodiments, the system (100) comprises one channel, two channels, three channels, four channels, five channels, six channels, seven channels, eight channels, nine channels, 10 channels, or more than 10 channels. The tip (112) of the distal portion (110) of the cannula system (100) is not limited to the shapes (e.g., rounded, circular) described and shown herein.

The emanating sources (401) occupy the treatment position(s) for a certain length of time, or dwell time. The dwell time at the various treatment positions may be the same or different.

In some embodiments, the emanating source (401) travels to each treatment position (118) in its respective channel (160). In some embodiments, the emanating source (401) travels to selected treatment positions (118) in its respective channel (160). In some embodiments, the emanating source (401) travels to each treatment position (or each selected treatment position (118)) sequentially (e.g., treatment position 1, then treatment position 2, then treatment position 3, etc., or treatment position 5, then treatment position 4, then treatment position 3, etc.) or in a selected order (e.g., treatment position 1, then treatment position 5, then treatment position 3, etc.).

Without wishing to limit the present invention to any theory or mechanism, it is believed that the summation of the treatment positions, each with a dwell time (same amount of time or different amounts of time) may add up in an overlapping fashion to achieve a more uniform dose delivered; this dose delivered may be similar to that of an annulus seed or a ring of seeds.

Figure 6A:
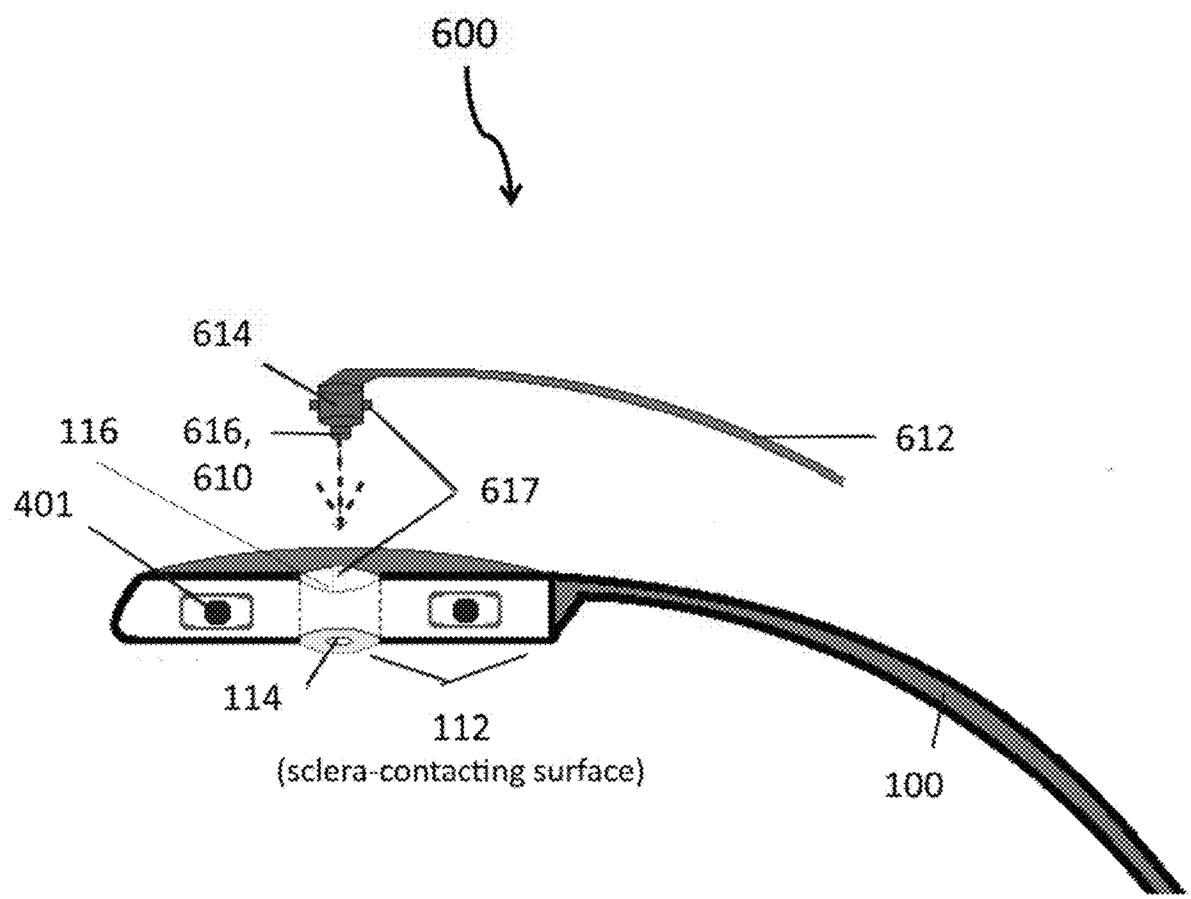
FIG. 6A shows a side view of a light source assembly.
Figure 6B:
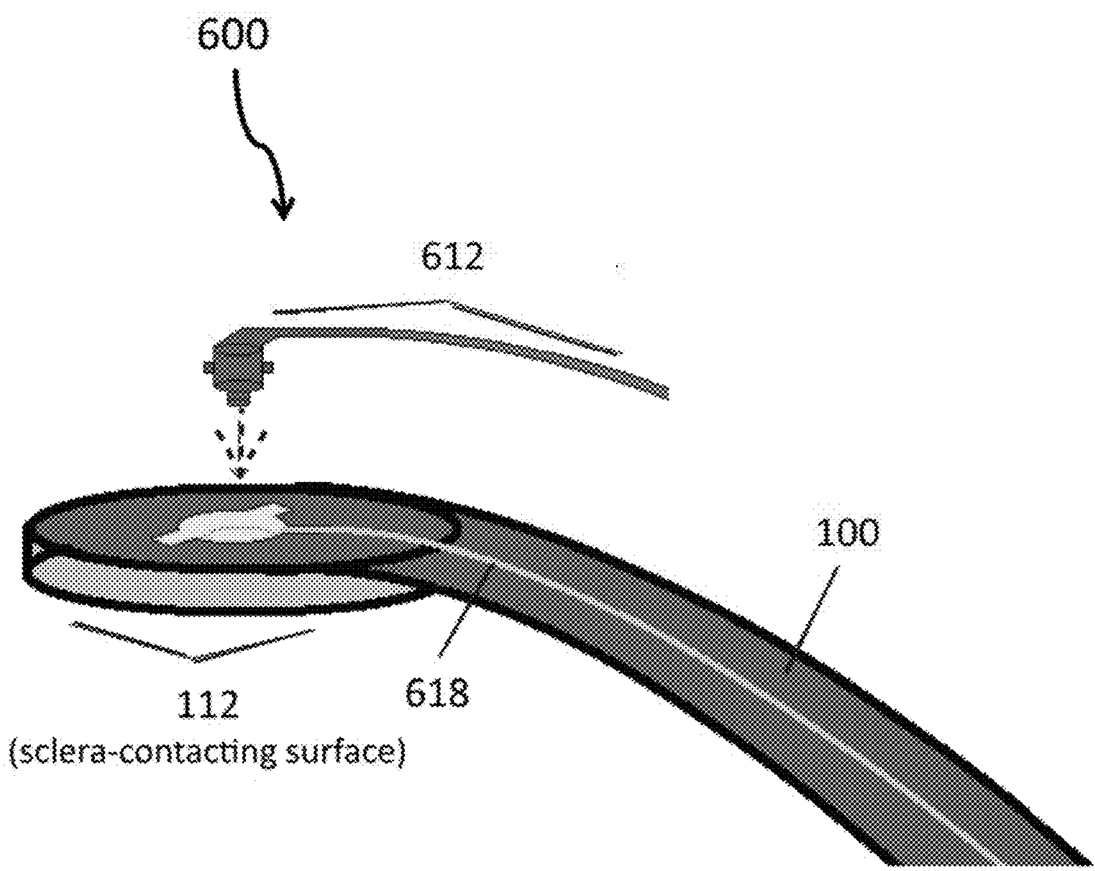
FIG. 6B shows a perspective view of a light source assembly.
Figure 6C:
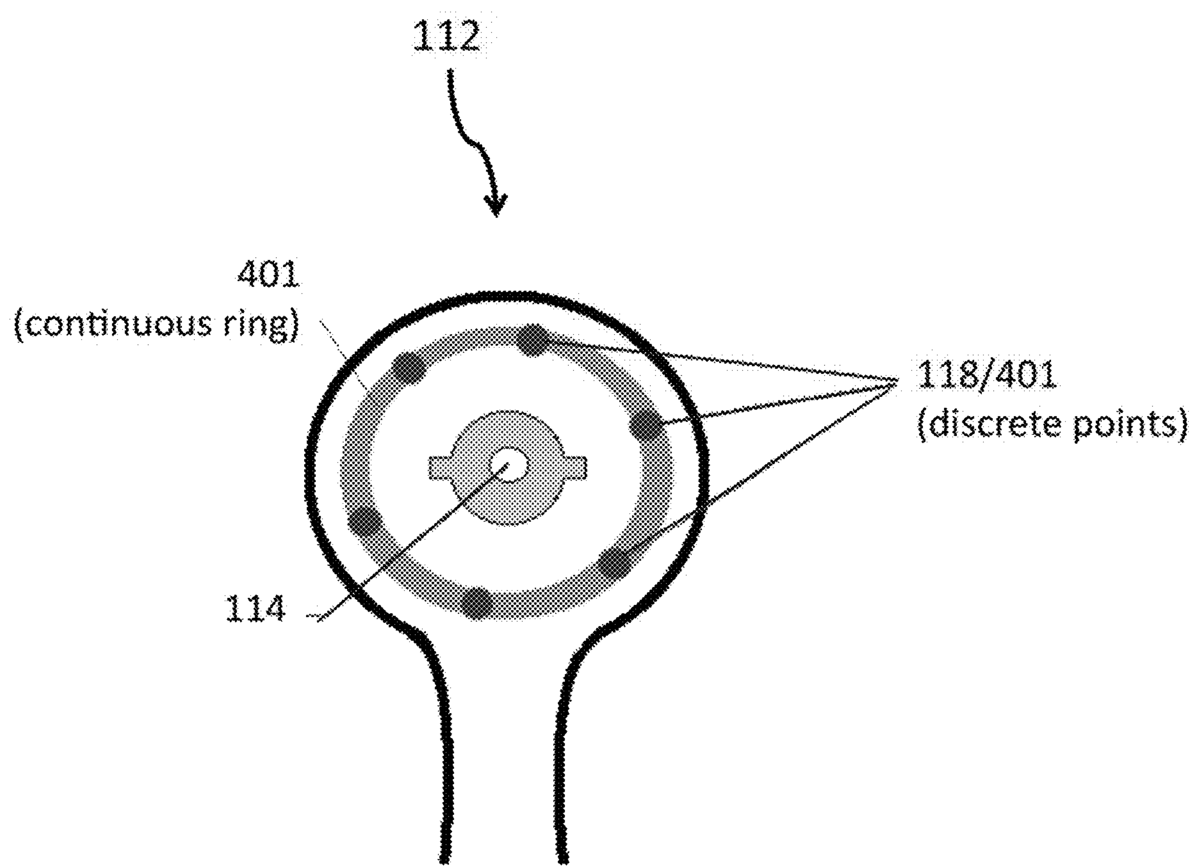
FIG. 6C shows a bottom view of the light source assembly of FIG. 6B (as viewed from the bottom (or sclera-contacting surface) of the tip of the distal portion of the cannula system). The emanating source may be discrete units or a continuous ring (or partial ring, not shown). The emanating sources are not limited to these configurations.
Figure 7A:
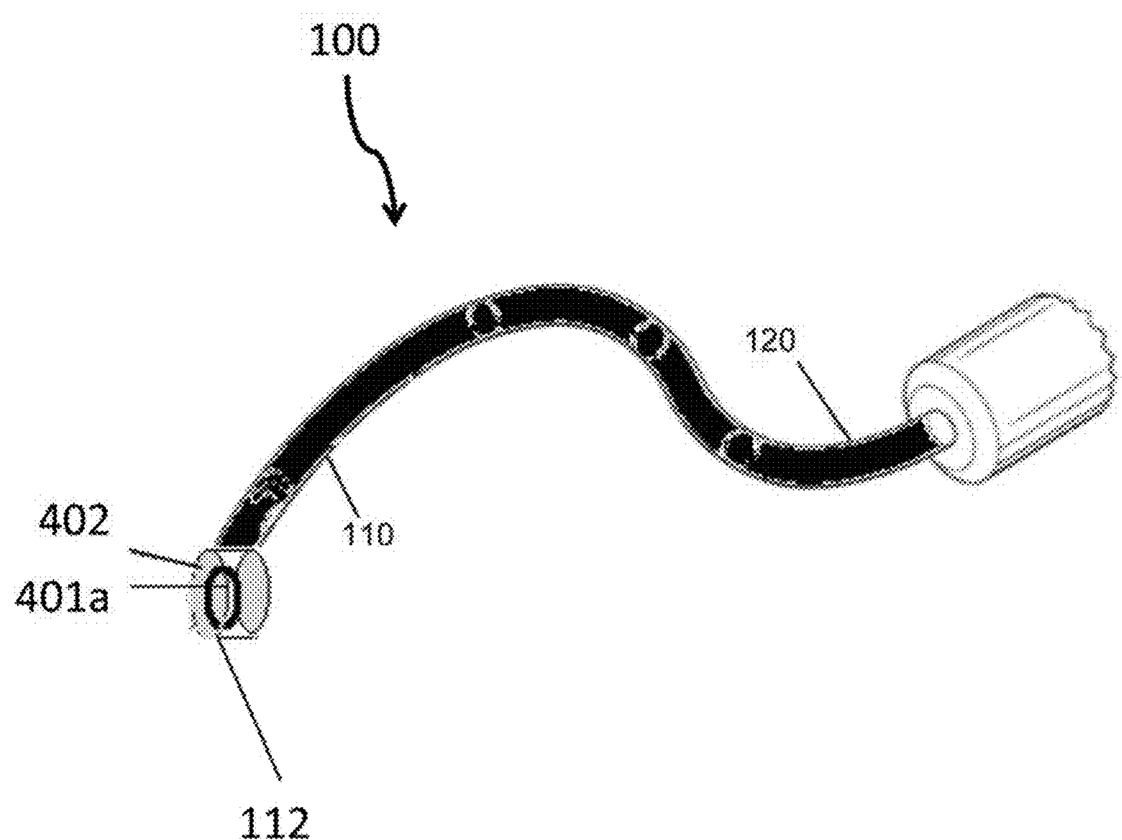
FIG. 7A shows the annulus-shaped emanating source at the tip of a cannula system.
Figure 7B:
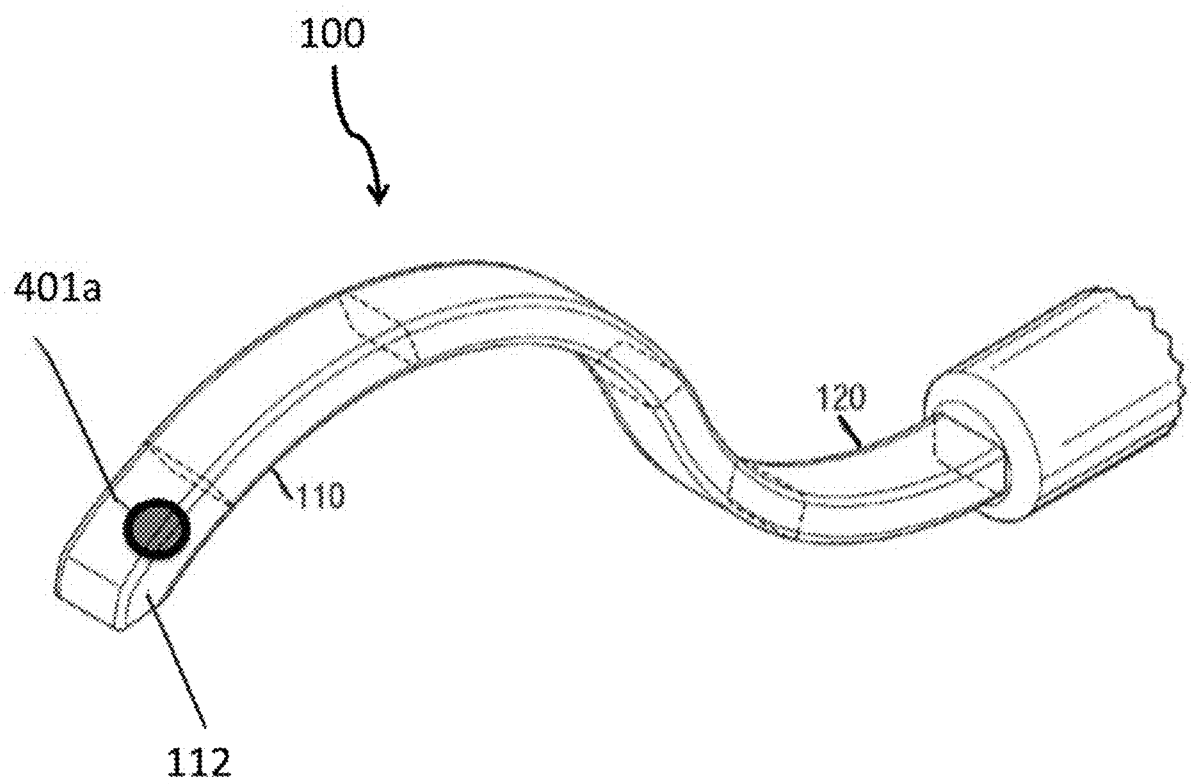
FIG. 7B shows an emanating source with an annulus-like radiation profile disposed in the tip of the cannula system (100).

For example, in reference to figures from provisional application 61/877,765, FIG. 6C shows the relative dose distribution for a system wherein an emanating source (401) (e.g., Sr 90) occupies six treatment positions (arranged radially on a 4 mm diameter circle thus spaced a distance of about 2 mm from a center point (113)) in a plane 2 mm away from the target plane (the treatment positions are in a circle-shaped channel (160) in the tip (112) of a cannula system (100) similar to that shown in FIG. 5A). For reference, FIG. 6A shows a schematic diagram of six treatment positions (arranged radially on a 4 mm diameter circle thus spaced a distance of about 2 mm from a center point (113)) in a plane 2 mm away from the target plane. FIG. 6B shows the relative dose distribution for a system with a single fixed source (emanating source (401)) (e.g., Sr 90). The distance between the source midpoint and the target center is 2 mm away from the center of a target. For reference, FIG. 6D and FIG. 6E show a side view and a top cross sectional view, respectively, of a single source (a four-beaded Sr-90 source) against detectors at various distances from the source (e.g., 1.0 mm, 1.5 mm, 2.0 mm, 2.5 mm, 3.0 mm, and 3.5 mm; the data used to compare with the six-position source above is the 2.0 mm distance). FIG. 6F shows dose distribution as surface plots and iso-dose lines (in Gy/min mCi) for the source of FIG. 6D and FIG. 6E at the 2.0 mm distance from the source midpoint.

In reference to figures from provisional application 61/877,765, FIG. 6G and FIG. 6H show the 3D dose distribution of a generally annulus-like distribution of emanating sources (401) (top) and a linear-shaped emanating source (401) (see configuration in FIG. 6D) (bottom) at 0.25 mm from the source (FIG. 6G) and 2.0 mm from the source (FIG. 6H). At the 2 mm distance, the annulus-like distribution gives a more uniform dose across the diameter.

In reference to figures from provisional application 61/877,765, for comparison, FIG. 6I shows the 3D dose distribution (top) and iso-dose lines (middle) of a ring-shaped (annulus-like) emanating source (401) (bottom); FIG. 6J shows the 3D dose distribution (top) and iso-dose lines (middle) of a horseshoe-shaped emanating source (401) (bottom). The horseshoe-shaped emanating source (401) approximates an annulus-like shape.

The present invention is not limited to emanating sources (401) comprising Sr 90; other isotopes may be used (e.g., Y-90, Iodine-125, Cesium-131, Cesium-137, Ir-192, Ru-106, combinations of isotopes), and the emanating sources (401) are not limited to any particular form of radiation (e.g. emitters of alpha, beta, or gamma).

In some embodiments, an afterloading system (700) sends one or more emanating sources (401) through the channels (160). For example, the afterloading system (700) may comprise multiple guide tubes (720), e.g., one guide tube (720) for each channel (160) in the cannula system (100).

The tip (112) of the distal portion (110) of the cannula system (100) may be constructed in a variety of shapes and sizes. For example, in some embodiments, the tip (112) of the distal portion (110) of the cannula system (100) is rounded. In some embodiments, the tip (112) of the distal portion (110) of the cannula system (100) is an annulus or a variation thereof (e.g., partial annulus, a horseshoe shape, etc.). For example, FIG. 4A. FIG. 4B, FIG. 5, FIG. 6A, FIG. 6B, FIG. 6C and FIG. 7A show the tip (112) having a generally annulus shape. The tip (112) may be any appropriate shape to accommodate the emanating source (401) and/or channels (160) and/or singular or multiple treatment positions (118).

In some embodiments, the emanating source (401) is directed through one or more channels (160) to one or more treatment positions (118) that in summation deliver a dose to the target approximating that emanating from an annulus (or partial annulus).

Light Source Assembly

In some embodiments, the cannula system (100) comprises a light source. For example, in some embodiments, the cannula system (100) comprises a light source or in some embodiments, the cannula system (100) comprises a means of emitting light from a distant source (e.g., a "light source emitter component (610)", e.g., a fixture at the end of a fiber optic cable) connected, for example, via a fiber optic cable or light pipe (612). The light source (e.g., light source emitter component (610)) may be positioned in any appropriate place on the cannula system (100). For example, in some embodiments, the light source (e.g., light source emitter component (610)) is positioned in the center of the distal end (112) of the distal portion (110) of the cannula system (100), e.g., as shown in FIG. 4A and FIG. 40. The light source (e.g., light source emitter component (610)) may be incorporated into the cannula system (100) or may be a separate system.

In some embodiments, the cannula system (100) comprises a light source assembly (600), wherein the light source emitter component (610) is incorporated into the light source assembly (600). For example, FIG. 6A-6C show a fiber optic cable (612) with a light source plug (614) disposed on its end. The fiber optic cable (612) may be connected to an external light source.

In some embodiments, the light source emitter component (610) is incorporated into the light source plug (614). For example, in some embodiments, the light source emitter component (610) is disposed on the tip (616) of the light source plug (614). As shown in FIG. 6A, the light source plug (610) and light source emitter component (610)/tip (616) of light source plug (614) are adapted to engage (e.g., slide into) a light source plug compartment (116) disposed in the tip (112) of the distal portion (110) of the cannula system (100). In some embodiments, the light source plug compartment (116) is disposed in the center of the tip (112) of the distal portion (110) of the cannula system (100). In some embodiments, the light source plug compartment (116) is disposed in the center of the emanating sources (401) in the tip (112) of the cannula system (100) (see FIG. 6C). The placement and configuration of the light source plug compartment (116) is not limited to the positions and configurations shown herein.

In some embodiments, the tip (616) (e.g., light source emitter component (610)) of the light source plug (614) engages a light aperture (114) disposed on the bottom surface (e.g., the sclera-contacting surface) of the tip (112) of the cannula system (100). The light aperture (114) may allow the tip (616) (e.g., light source emitter component (610)) of the light source plug (614) to contact the sclera. This may allow transmission of light through the sclera.

In some embodiments, the light source plug (614) is secured in the light source plug compartment (116) via a locking mechanism, e.g., a luer lock or other appropriate type of lock. In some embodiments, a groove (618) is disposed in the cannula system (100), e.g., in the distal portion (110) of the cannula system (100) adapted to engage the fiber optic cable (612) (see FIG. 6B).

As shown in FIG. 6C, the emanating source (401) may comprise one or more discrete seeds, for example arranged in an annulus configuration (e.g., equidistant from the center) or a continuous ring. The emanating source (401) configuration is not limited to the aforementioned configurations. For example, the discrete seeds may not necessarily be arranged equidistant from the center, or the discrete seeds may not form an annulus configuration, or the continuous ring may be a partial ring or variation thereof.

In some embodiments, a prism (613) is disposed at the end of the fiber optic cable or light pipe (612). Without wishing to limit the present invention to any theory or mechanism, it is believed that the prism (613) may allow for transmission of light at a right angle from the fiber optic cable or light pipe (612) through the aperture (114).

Emanating Source Shapes and Radiation Emission Shapes

The present invention features emanating sources (401) and emanating source systems. An emanating source (401) may refer to an isotope/source that emanates or emits radiation (see FIG. 12). An emanating source (401) may be a stand-alone radiation source, e.g., radioactive isotope or radioactive isotope complexed with a carrier such as alloyed or a ceramic carrier; or the emanating source (401) may comprise a jacket (402) (e.g., gold, titanium, stainless steel, platinum) or other encasement (forming, for example, a "radionuclide brachytherapy source" (RBS), e.g., seed). In some embodiments, the emanating source (401) comprises a radiation shaper (406) to shape the emitted radiation from the emanating source (401). The emanating sources (401) or emanating source systems of the present invention may be used to treat wet AMD or any other appropriate disease or condition (e.g., lesion, tumor, etc.).

In some embodiments, the emanating source (401) is attached to a cannula (e.g., a cannula of the present invention or other cannula, e.g., a rod, tube, a solid stick, a hollow or partially hollow stick, a curved cannula, etc.); for example, the cannula system (100) of the present invention may comprise an emanating source (401). In some embodiments, the emanating source (401) is a stand-alone unit (e.g., is not attached to a cannula).

In some embodiments, the emanating source (401) has a radiation emission shape (406) (e.g., shape of radiation emitted/shape of radiation at the target) of an annulus shape (or similar, e.g., a partial annulus), e.g., the emanating source (401) is an "annulus emanating source" (401*a*). In some embodiments, the emanating source (401) (e.g., annulus emanating source (401*a*)) is a stand-alone unit (e.g., is not attached to a cannula).

In some embodiments, the emanating source (401) (e.g., annulus emanating source (401*a*)) is attached to a cannula (e.g., a cannula of the present invention or other cannula, e.g., a rod, tube, a solid stick, a hollow or partially hollow stick, a curved cannula, etc.); for example, the cannula system (100) of the present invention may comprise an annulus emanating source (401*a*). In some embodiments, the emanating source (401) (e.g., annulus emanating source (401*a*)) is attached to the distal end of a cannula with a solid core, or a solid rod, or an applicator that is not a cannula. In some embodiments, the emanating source (401) (e.g., annulus emanating source (401*a*)) is attached to the distal end of a solid rod of stainless steel. In some embodiments, the emanating source (401) (e.g., annulus emanating source (401*a*)) is attached to the distal end of a cannula with the Inner Diameter comprised of a light pipe.

In some embodiments, the emanating source (401) (e.g., annulus emanating source (401*a*)) is in the shape of an annulus (e.g., ring) (or similar shape, e.g., partial annulus, horseshoe shape, half-pipe shape, etc.), or a variation of an annulus (e.g., a square with a hollow center, a rectangle with a hollow center, another geometric or symmetrical shape (rotationally symmetrical shapes) with a hollow center, etc.). In some embodiments, the emanating source (401) (e.g., annulus emanating source (401*a*)) is not necessarily in the shape of an annulus, but the overall radiation flux/radiation emission shape (406) of the emanating source (401) is that of an annuls or similar shape. For example, in some embodiments, the emanating source (401) comprises one or multiple wires that together form a generally annulus-like radiation emission shape (406). Or, in some embodiments, multiple discrete emanating source (401) points have a cumulative annulus-like radiation emission shape (406). The emanating sources (401) are not limited to the configurations described herein.

Without wishing to limit the present invention to any theory or mechanism, it is believed that for beta radiation, or other radiation (e.g., gamma), the shape of an annulus may allow for a generally flat dosimetry across a broader diameter. Shapes approximating an annulus, e.g., a square made of four rectangular seeds, three, four, five, or six (or more) seeds evenly spaced around in a circle, a partial annulus (horseshoe), etc., may have similar dosimetry. Such dosimetry may provide improved dose homogeneity across a target (e.g., lesion, tumor), for example the dose may be substantially uniform across a target (e.g., there is an absence of a dose hot spot center and the edges of the target may receive a more equivalent dose as at the center). In some embodiments, the annulus emanating source (401*a*) (or similar shape) may provide a more uniform dose distribution throughout the depth of the target. In some embodiments, the shape of the emanating source is not necessarily an annulus, but the resulting radiation flux at one of the surfaces of the emanating source is in an annulus configuration (e.g., a ring of discrete seeds, a source combined with a radiation shaper, etc.). In some embodiments, at one of its surfaces, the emanating source has a resulting outwardly projecting radiation flux that comprises a centrally located attenuation zone and a surrounding peripheral radiation zone. The surrounding peripheral radiation zone may be continuous or may be discrete regions (e.g., formed by discrete radiation units/seeds) of outwardly projecting radiation that surrounds the attenuation zone. Further, as discussed above, an emanating source (401) may be an isotope/source itself that emanates or emits radiation (e.g., an annular shaped isotope seed). In some embodiments, an emanating source (401) may comprise a jacket (402) (e.g., gold, titanium, stainless steel, platinum) or other encasement which has an isotope embedded within, wherein the isotope seed itself does not provide for an attenuation zone but the jacket is configured and constructed to provide for the resulting attenuation zone at the surface of the emanating source at the surface of the emanating source (e.g., the jacket comprising a centrally disposed radiation shaper). In some embodiments, the jacket and the seed embedded therein are configured and constructed to provide for the resulting attenuation zone at the surface of the emanating source.

In reference to figures from provisional application 61/877,765, FIG. 13A shows a comparison of dose rates in a target region for several emanating source (401) designs. The ring (annulus) source has a more homogenous dose distribution over the target zone as compared to the disc source. FIG. 13B also shows a comparison of dose rates in a target region for several emanating source (401) designs: (a) 4 active seeds arranged side by side; (b) 4 seeds arranged side by side wherein only the outer 2 seeds are active; and (c) 4 active seeds arranged on the circumference of a square. For the "4 active seeds on the circumference of a square, the maximum target dose rate per activity was nearly half that of the other two arrangements. And, the dose distribution over the target zone was more homogeneous for the "4 active seeds lying on the circumference of a square" source as compared to the other two arrangements.

Figure 10:
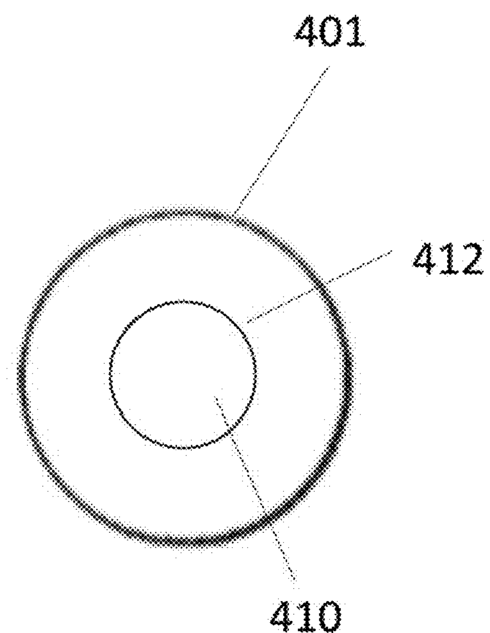
FIG. 10 shows examples of emanating source shapes (or radiation emission shapes).
Figure 10:
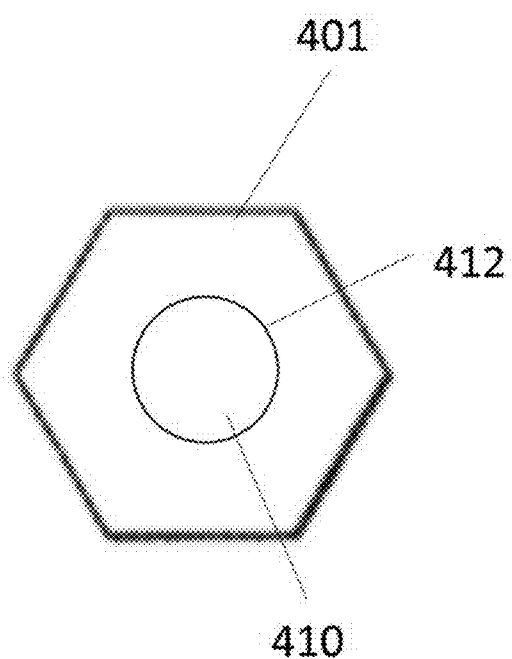
Figure 11:
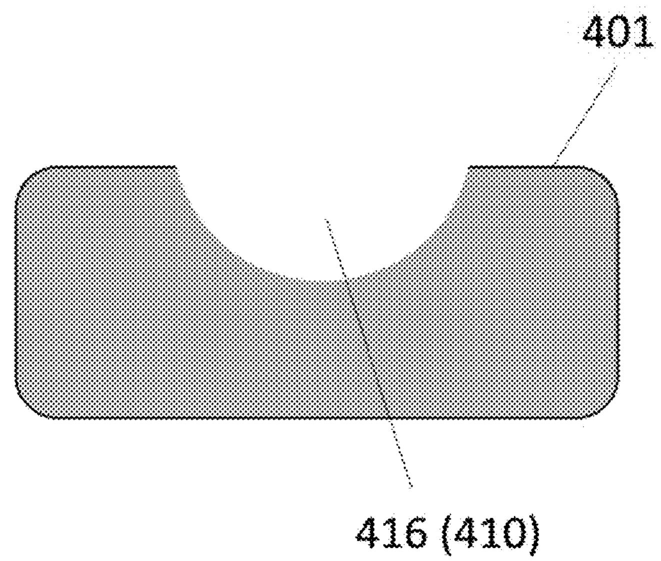
FIG. 11 shows side cross sectional views of two examples of emanating source configurations, one with an indentation and one with a hole.
Figure 11:
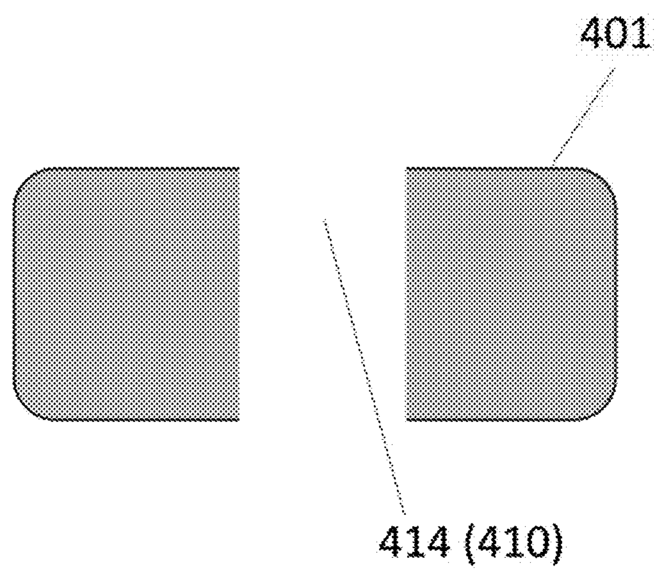

In reference to figures from provisional application 61/877,765, FIG. 10 shows an annulus-shaped emanating source. The dose to the target is generally uniform across the target's width. The annulus-shaped emanating source may be housed in a jacket (402), e.g., a disk-shaped jacket. FIG. 11A shows the annulus-shaped emanating source within a jacket (402) disposed at the tip (112) of the cannula system (100). FIG. 11B shows the annulus-shaped emanating source disposed in the cannula system (100). The annulus-shaped emanating source is not limited to use with a cannula system of the present invention. The annulus-shaped emanating source may be used alone or in combination with any other appropriate cannula or device.

Figure 12:
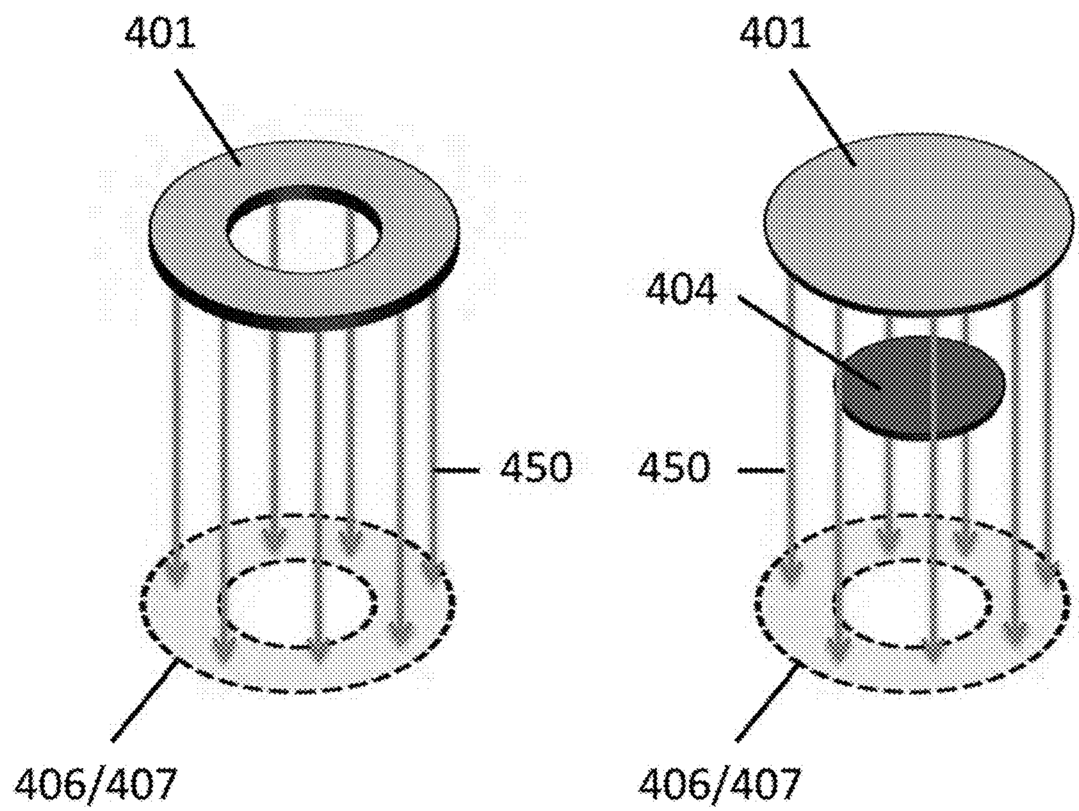
FIG. 12 shows radiation flux for two annulus emanating sources: (a) an annulus-shaped emanating source and a disc-shaped emanating source paired with a radiation shaper. The resulting radiation emission shape is that of an annulus configuration.

In some embodiments, a radiation shaper (404) is used to shape the radiation emitted from the emanating source (401). In some embodiments, the emanating source (401) is not annulus shaped, but the radiation shaper (404) creates an annulus-shaped radiation emission shape (406). Thus, while the emanating source (401) is not annulus-shaped, the effect of the radiation shaper (404) is still an annulus-shaped emanating source (401). FIG. 12 shows a disk-shaped emanating source (401*b*)) and a rounded radiation shaper (404). The radiation shaper (404) blocks the radiation (or a portion thereof) in its path (e.g., limiting the radiation traveling to the target).

As previously discussed, in some embodiments, the emanating source (401) may be in the shape of an annulus or similar. In some embodiments, the emanating source (401) is constructed in any other shape but is paired with a radiation shaper (404) that shapes the radiation that reaches the target (the radiation emission shape (406)) in the shape of an annulus or similar (or the summation of the discrete points of radiation is effectively similar to an annulus or similar shape). The emanating sources (401) and emanating source systems are not limited to the aforementioned configurations. For example, in some embodiments, the emanating source (401) is in the shape of a rotationally symmetrical shape (see FIG. 9A).

In some embodiments, the emanating source (401) is complexed with a carrier. In some embodiments, the emanating source (401) is complexed with a radiation shaper, and the emanating source (401) and radiation shaper are together housed in a jacket or encasement (e.g., stainless steel, gold, or titanium). In some embodiments, the emanating source (401) is housed in a jacket or encasement and a radiation shaper is disposed external to the jacket (402) or encasement. In some embodiments, "active material" refers to the emanating source. In some embodiments, "active material" refers to the emanating source complexed with a carrier.

In some embodiments, the emanating source (401) comprises an attenuation zone (410) that has either reduced or eliminated radiation emitted from the region. For example, in some embodiments, the emanating source (401) comprises an attenuation zone (410), wherein the attenuation zone (410) is a hole. The hole (414) may create an annulus-shaped emanating source (401). In some embodiments, the attenuation zone (410) is an indentation (416). In some embodiments, the attenuation zone (410) comprises a shield for shielding or partially shielding radiation emitted from the attenuation zone (410). Again, the attenuation zone (410) may be achieved by combining a radiation shaper (404) in combination with the emanating source (401), thereby shaping the radiation emission shape (406). Non-limiting examples of such emanating sources (401) are shown in FIG. 10. The emanating sources (401) are not limited to the shapes and configurations shown herein.

Figure 9A:
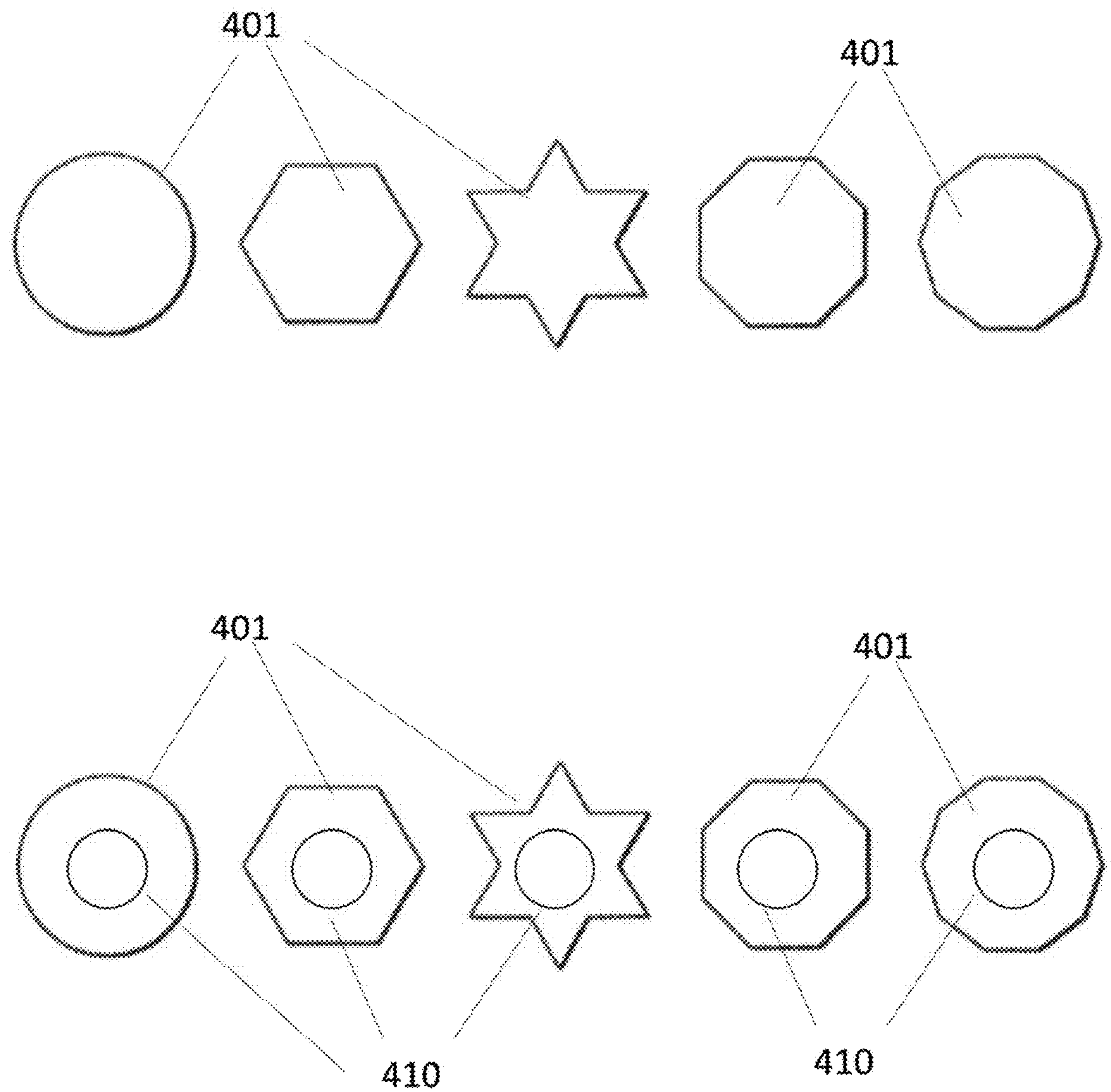
FIG. 9A shows examples of emanating sources (or radiation emission shapes).
Figure 9B:
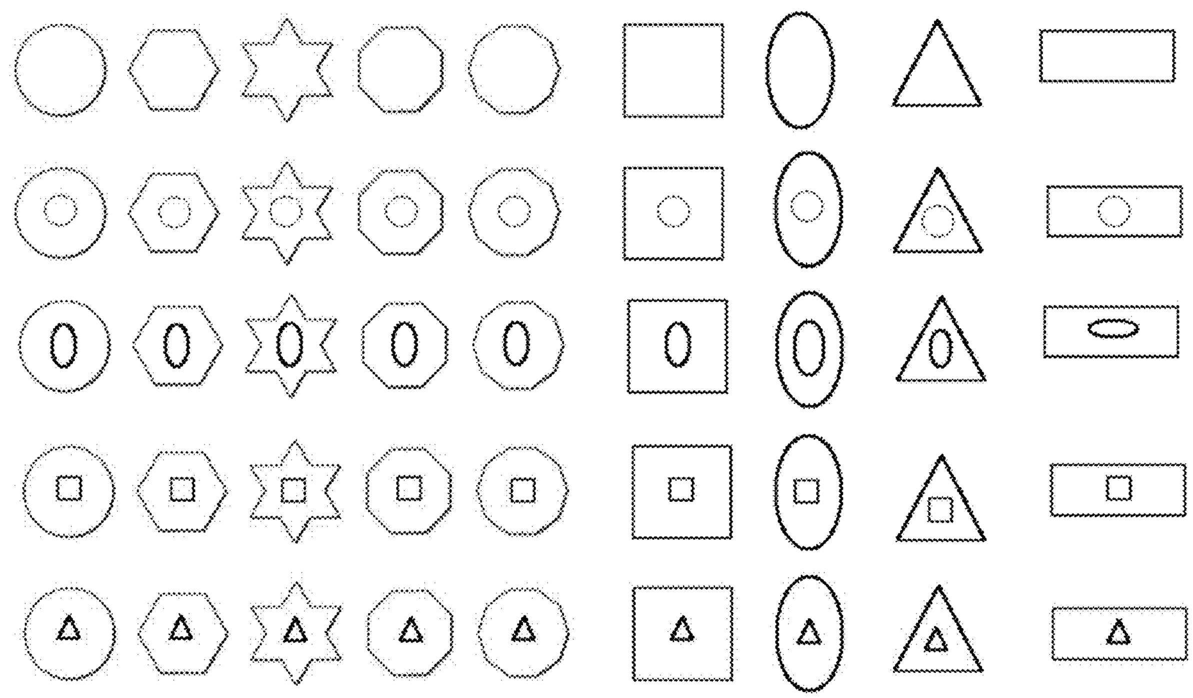
FIG. 9B shows additional examples of emanating sources (or radiation emission shapes) with attenuation zones.

FIG. 9B (and FIG. 9A) shows examples of possible shapes of the emanating sources (401) or the radiation emission shape (406). The attenuation zone (410) is not limited to a circular shape (or a square shape, triangular shape, oval shape, etc.).

The attenuation zone (410) may allow the emanating source (401) to achieve a substantially flat dose rate both at the central area of the target as well as across the diameter of the target (as compared to a disk-shaped emanating source/radiation emission shape).

In some embodiments, the dose that is emitted from the attenuation zone (410) is about 10% less than the dose emitted from the outer edge (412) of the attenuation zone (410). In some embodiments, the dose that is emitted from the attenuation zone (410) is about 15% less than the dose emitted from the outer edge (412) of the attenuation zone (410). In some embodiments, the dose that is emitted from the attenuation zone (410) is about 20% less than the dose emitted from the outer edge (412) of the attenuation zone (410), In some embodiments, the dose that is emitted from the attenuation zone (410) is about 25% less than the dose emitted from the outer edge (412) of the attenuation zone (410). In some embodiments, the dose that is emitted from the attenuation zone (410) is about 30% less than the dose emitted from the outer edge (412) of the attenuation zone (410). In some embodiments, the dose that is emitted from the attenuation zone (410) is about 40% less than the dose emitted from the outer edge (412) of the attenuation zone (410). In some embodiments, the dose that is emitted from the attenuation zone (410) is about 50% less than the dose emitted from the outer edge (412) of the attenuation zone (410). In some embodiments, the dose that is emitted from the attenuation zone (410) is about 60% less than the dose emitted from the outer edge (412) of the attenuation zone (410). In some embodiments, the dose that is emitted from the attenuation zone (410) is about 70% less than the dose emitted from the outer edge (412) of the attenuation zone (410). In some embodiments, the dose that is emitted from the attenuation zone (410) is about 80% less than the dose emitted from the outer edge (412) of the attenuation zone (410). In some embodiments, the dose that is emitted from the attenuation zone (410) is about 90% less than the dose emitted from the outer edge (412) of the attenuation zone (410). In some embodiments, the dose that is emitted from the attenuation zone (410) is about 100% less than the dose emitted from the outer edge (412) of the attenuation zone (410).

As previously discussed, the emanating source (401) is not limited to the configurations described herein. For example, in some embodiments, the emanating source (401) comprises one or multiple wires that together form a generally annulus-like radiation emission shape (406). Or, in some embodiments, multiple discrete emanating source (401) points have a cumulative annulus-like radiation emission pattern (radiation emission shape).

In some embodiments, the attenuation zone (410) is proportional in size to the remaining area of the emanating source (401) shape (or radiation emission shape (406)) such that the dosimetric profile delivers a substantially flat dose rate over the entire area contained by the emanating source (401) (including over the attenuation zone (410), which may have reduced or absent radiation emission as compared to the remaining area of the emanating source (401)/radiation emission shape (406)).

In reference to figures from provisional application 61/877,765, FIG. 13A shows modeled emanating sources (401), e.g., a disc and rings with an outer diameter of 4 mm and a thickness of 0.1 mm. The rings had inner diameters of 2.0, 3.0, 3.5 and 3.6 mm. As the inner diameters increased (holes were bigger), there was more homogeneity of dose distribution. The emanating source (401) may be customized according to lesion size and depth. For example, the emanating source (401) may comprise a ring with an inner diameter greater than 3.6 mm or less than 2.0 mm, the emanating source (401) may have a larger or smaller thickness than 0.1 mm, the emanating source (401) may have a larger or smaller outer diameter than 4 mm, etc. FIG. 17 shows a disc-shaped emanating source (401) (left) and a ring-shaped emanating source (401) (right), e.g., an annulus-shaped emanating source (401). These configurations were used to calculate the dosimetry shown in FIG. 13A.

Figure 8:
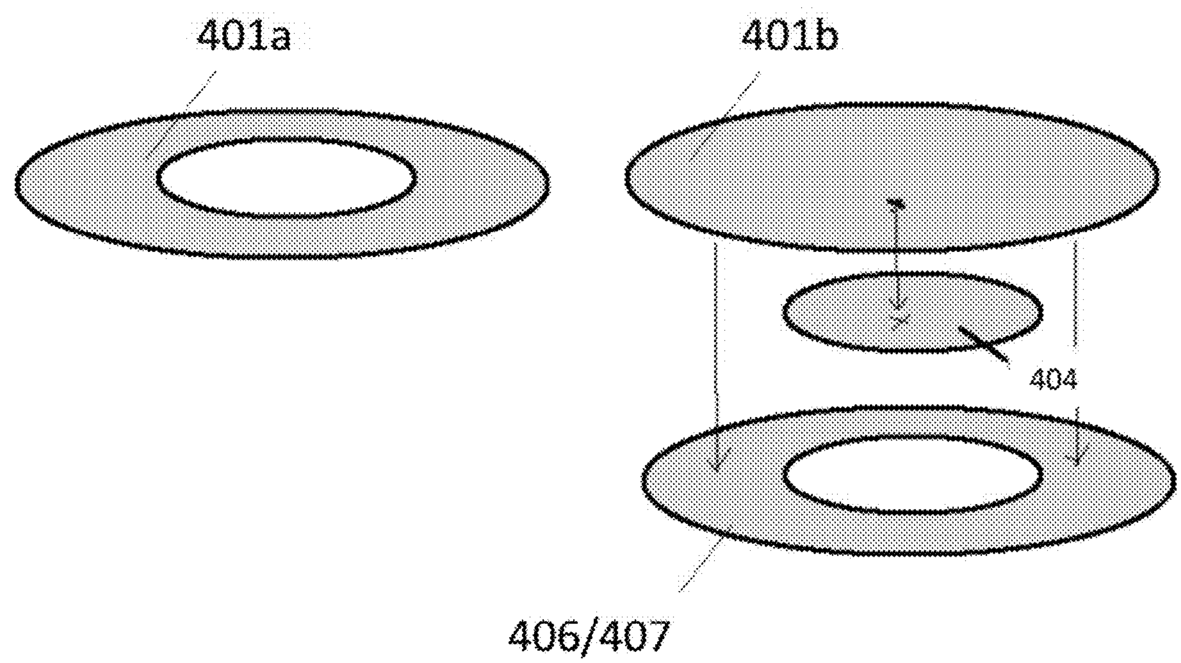
FIG. 8 shows an annulus-shaped emanating source and an emanating source that has an annulus-shaped radiation emission shape because of the radiation shaper positioned between the target and the emanating source.

FIG. 8 shows radiation flux (450) for two annulus emanating sources: (a) an annulus-shaped emanating source and a disc-shaped emanating source paired with a radiation shaper. The resulting radiation emission shape (406) is that of an annulus configuration.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed:

1. A brachytherapy system comprising a cannula system (100) for insertion into a potential space between a sclera and a Tenon's capsule of an eye of a patient, the cannula system (100) comprises a distal portion (110) with a tip (112), one or more channels (160) that extend through the cannula system (100) to the tip (112), the one or more channels (160) comprising at least one treatment position (118) in the tip (112) for one or more emanating sources (401), and a light source assembly (600), wherein the light source assembly (600) comprises a fiber optic cable or light pipe (612) operatively connected to an external light source, a light source plug (614) is disposed on an end of the fiber optic cable or light pipe (612), a light source emitter component (610) is incorporated into the light source plug (614), the light source plug (610) and light source emitter component (610) are adapted to engage a light source plug compartment (116) disposed in the tip (112) of the distal portion (110) of the cannula system (100), wherein the light source plug (614) and light source emitter component (610) engage a light aperture (114) disposed on a bottom surface of the tip (112) of the cannula system (100).

2. The system of claim 1, wherein the one or more emanating sources (401) are configured to be directed through the one or more channels (160) to one or more treatment positions (118) to deliver a dose to the target that approximates a dose emanating from an annulus.

3. The system of claim 1, wherein the tip (112) of the cannula system (100) is disk-shaped.

4. The system of claim 1, wherein the one or more emanating source (401) is an annulus or a partial annulus.

5. The system of claim 1, wherein the one or more emanating source (401) is linear.

6. The system of claim 1, wherein the one or more emanating source (401) comprises one or more discrete seeds.

7. The system of claim 6, wherein the one or more discrete seeds comprises a plurality of discrete seeds are arranged in an annulus or partial annulus configuration.

8. The system of claim 1, wherein the one or more emanating sources (401) comprises a continuous ring or a portion of a ring.

9. The system of claim 1, wherein a prism is disposed at the end of the fiber optic cable or light pipe (612).

10. The system of claim 1, wherein the light source plug (614) is secured in the light source plug compartment (116) via a locking mechanism.

11. The system of claim 1, wherein a groove (618) is disposed in the cannula system (100) adapted to engage the fiber optic cable or light pipe (612).

12. The system of claim 1 further comprising an afterloading system (700) for delivering the one or more emanating sources (401) to the at least one treatment position (118).

13. The system of claim 12, wherein the afterloading system (700) comprises a guide tube (720) for each of the one or more channels (160) in the cannula system (100).

14. The system of claim 12, wherein the afterloading system (700) comprises: a vault (710) for storage of the one or more emanating sources (401), wherein the one or more emanating sources (401) are attached to an advancing means (722); a guide tube (720) extending from the vault (710), the guide tube (720) is removably attachable to the cannula system (100); and a source-drive mechanism (730) operatively connected to the advancing means (722), wherein the source-drive mechanism (730) is configured to advance the one or more emanating sources (401) through the guide tube (720) to the at least one treatment position (118) in the cannula system (100).

15. The system of claim 1, wherein the one or more emanating sources (401) are configured to provide a dose rate of between about 1 to 10 Gy/min to a target.

16. The system of claim 1, wherein the cannula system (100) comprises a proximal portion (120) connected to the distal portion (110) by an inflection point (130), the distal portion (110) has a radius of curvature between about 9 to 15 mm and an arc length between about 25 to 35 mm and the proximal portion (120) has a radius of curvature between about an inner cross-sectional radius of the cannula system (100) and about 1 meter.

* * * * *